(12) United States Patent
Bendix

(10) Patent No.: US 11,383,036 B2
(45) Date of Patent: Jul. 12, 2022

(54) MECHANISM FOR SEQUENTIAL DOSE DELIVERY

(71) Applicant: Novo Nordisk A/S, Bagsvaerd (DK)

(72) Inventor: Klaus Bendix, Vanloese (DK)

(73) Assignee: Novo Nordisk A/S, Bagsvaerd (DK)

( * ) Notice: Subject to any disclaimer, the term of this patent is extended or adjusted under 35 U.S.C. 154(b) by 260 days.

(21) Appl. No.: 16/066,969

(22) PCT Filed: Dec. 29, 2016

(86) PCT No.: PCT/EP2016/082875
§ 371 (c)(1),
(2) Date: Jun. 28, 2018

(87) PCT Pub. No.: WO2017/114921
PCT Pub. Date: Jul. 6, 2017

(65) Prior Publication Data
US 2019/0022316 A1 Jan. 24, 2019

(30) Foreign Application Priority Data
Dec. 30, 2015 (EP) .................................... 15203071

(51) Int. Cl.
*A61M 5/19* (2006.01)
*A61M 5/20* (2006.01)
(Continued)

(52) U.S. Cl.
CPC ............ *A61M 5/19* (2013.01); *A61M 5/2033* (2013.01); *A61M 5/2053* (2013.01);
(Continued)

(58) Field of Classification Search
CPC .... A61M 5/19; A61M 5/2053; A61M 5/3294; A61M 5/3298; A61M 5/315;
(Continued)

(56) References Cited

U.S. PATENT DOCUMENTS

| 4,609,371 A | 9/1986 | Pizzino |
| 2013/0245565 A1 | 9/2013 | Leak et al. |

(Continued)

FOREIGN PATENT DOCUMENTS

| CN | 103338801 A | 10/2013 |
| CN | 103687636 A | 3/2014 |

(Continued)

*Primary Examiner* — Tiffany Legette
*Assistant Examiner* — Antarius S Daniel
(74) *Attorney, Agent, or Firm* — Wesley Nicolas

(57) ABSTRACT

The present invention provides a drug delivery device (2, 3; 102) for sequential administration of substances, comprising a first variable volume reservoir (40a; 140a) holding a first substance and comprising a first outlet (41 a, 141 a) and a first displaceable wall (43a; 143a), a second variable volume reservoir (40b; 140b) holding a second substance and comprising a second outlet (41 b; 141 b) and a second displaceable wall (43b; 143b), a first wall actuation structure (65a, 70a, 75a, 77a; 177a) activatable to move the first displaceable wall (43a; 143a) and thereby expel a dose of the first substance through the first outlet (41 a; 141 a), a second wall actuation structure (65b, 70b, 75b, 77b; 177b) activatable to move the second displaceable wall (43b; 143b) and thereby expel a dose of the second substance through the second outlet (41 b; 141 b), and a drive structure (90; 190) for activating the first wall actuation structure (65a, 70a, 75a, 77a; 177a) and the second wall actuation structure (65b, 70b, 75b, 77b; 177b). The drive structure (90; 190) performs a predetermined movement during one sequential administration of the first substance and the second substance, the predetermined movement comprising a first part movement followed by a second part movement, and is configured to activate the first wall actuation structure (65a, 70a, 75a, 77a; 177a) during the first part movement and to activate the second wall actuation structure (65b, 70b, 75b, 77b; 177b) during the second part movement.

22 Claims, 14 Drawing Sheets

(51) Int. Cl.
*A61M 5/24* (2006.01)
*A61M 5/315* (2006.01)
*A61M 5/32* (2006.01)
*A61M 5/30* (2006.01)
*A61M 5/178* (2006.01)
*A61M 5/31* (2006.01)

(52) U.S. Cl.
CPC ........ *A61M 5/2066* (2013.01); *A61M 5/2448* (2013.01); *A61M 5/2466* (2013.01); *A61M 5/3007* (2013.01); *A61M 5/3155* (2013.01); *A61M 5/3158* (2013.01); *A61M 5/31596* (2013.01); *A61M 5/326* (2013.01); *A61M 5/3294* (2013.01); *A61M 5/3298* (2013.01); *A61M 2005/1787* (2013.01); *A61M 2005/3126* (2013.01)

(58) Field of Classification Search
CPC .............. A61M 5/3155; A61M 5/2466; A61M 5/31525; A61M 5/31596; A61M 5/2448; A61M 5/2066; A61M 2005/3126; A61M 2005/1787

See application file for complete search history.

(56) References Cited

U.S. PATENT DOCUMENTS

| | | | | |
|---|---|---|---|---|
| 2013/0267908 | A1* | 10/2013 | Leak | A61M 5/31563 |
| | | | | 604/191 |
| 2014/0303560 | A1* | 10/2014 | Yates | A61M 5/1452 |
| | | | | 604/154 |
| 2018/0193568 | A1* | 7/2018 | Hayton | A61M 5/31563 |

FOREIGN PATENT DOCUMENTS

| | | | | |
|---|---|---|---|---|
| GB | 2488735 A | * | 9/2012 | ......... A61M 5/2448 |
| WO | 2012072533 A1 | | 6/2012 | |
| WO | 2012072541 A1 | | 6/2012 | |
| WO | 2012160156 A2 | | 11/2012 | |
| WO | 2013072445 A1 | | 5/2013 | |
| WO | 2015181191 A1 | | 12/2015 | |

* cited by examiner

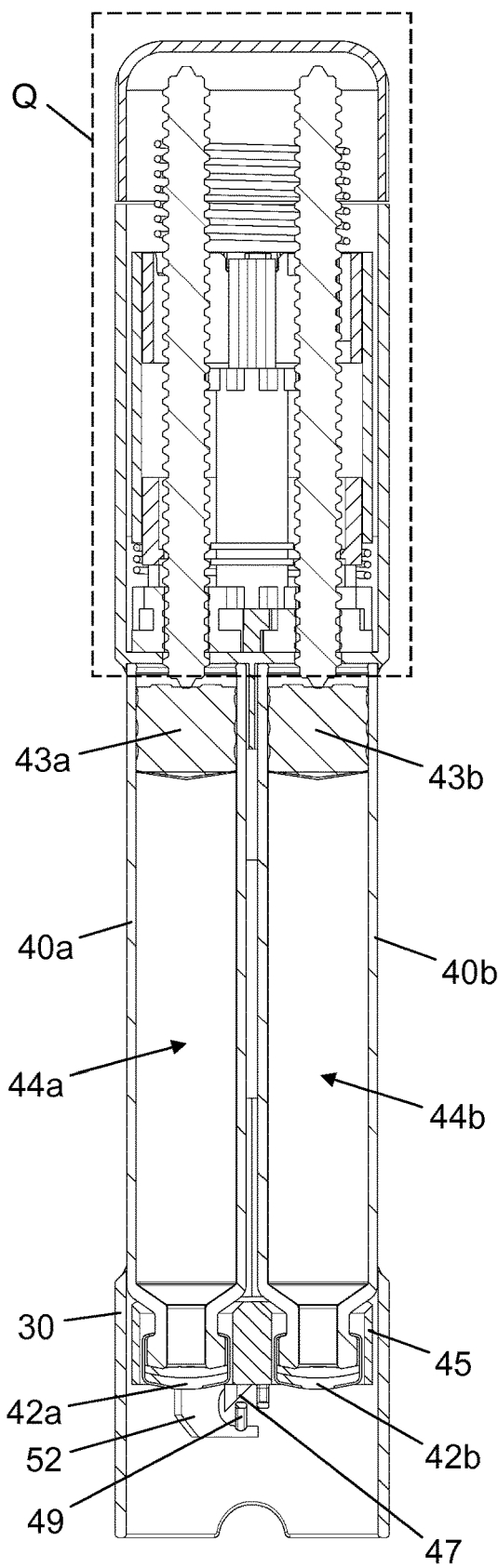
Fig. 2
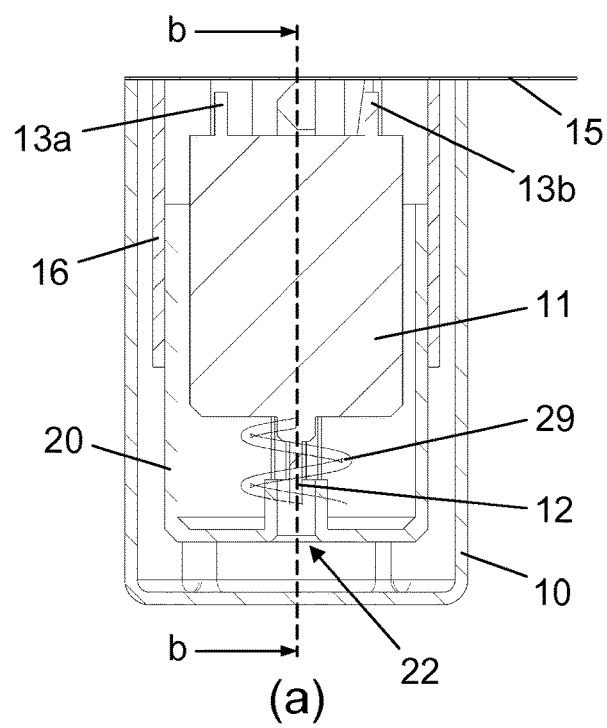
(a)
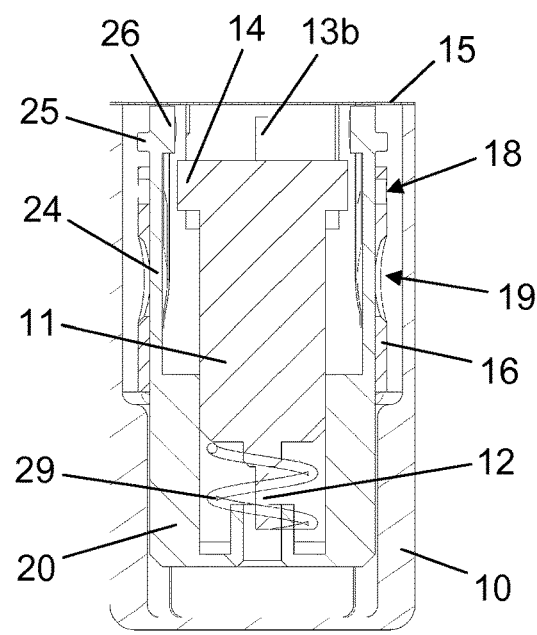
(b)
Fig. 3

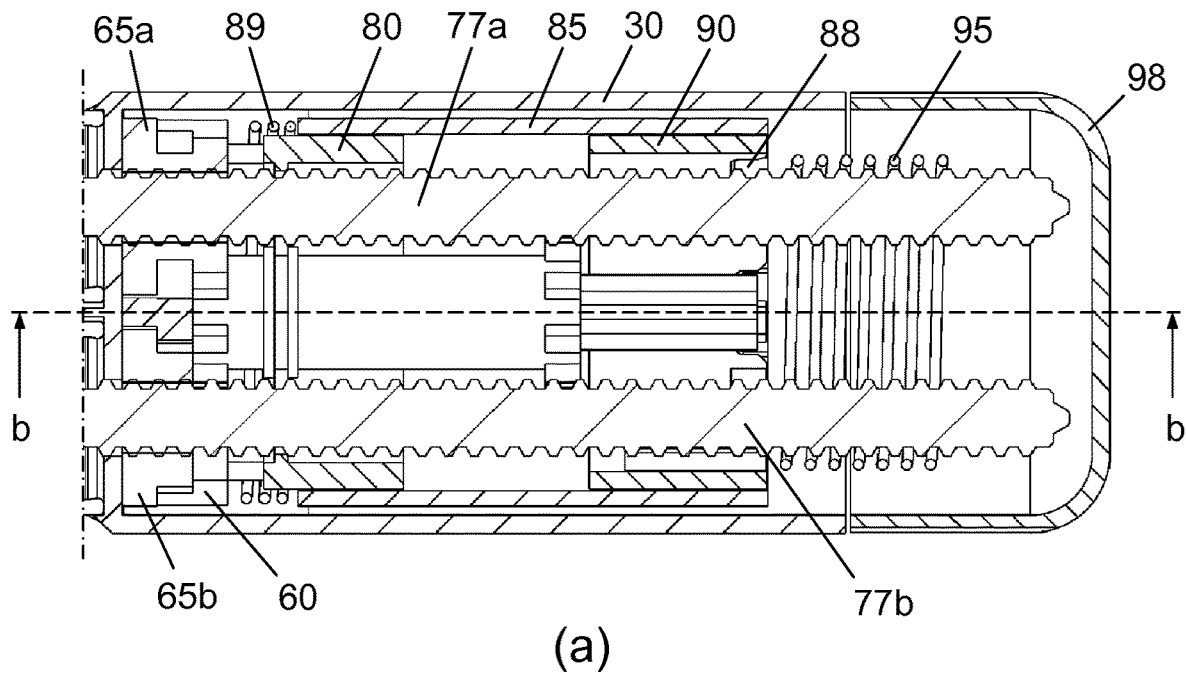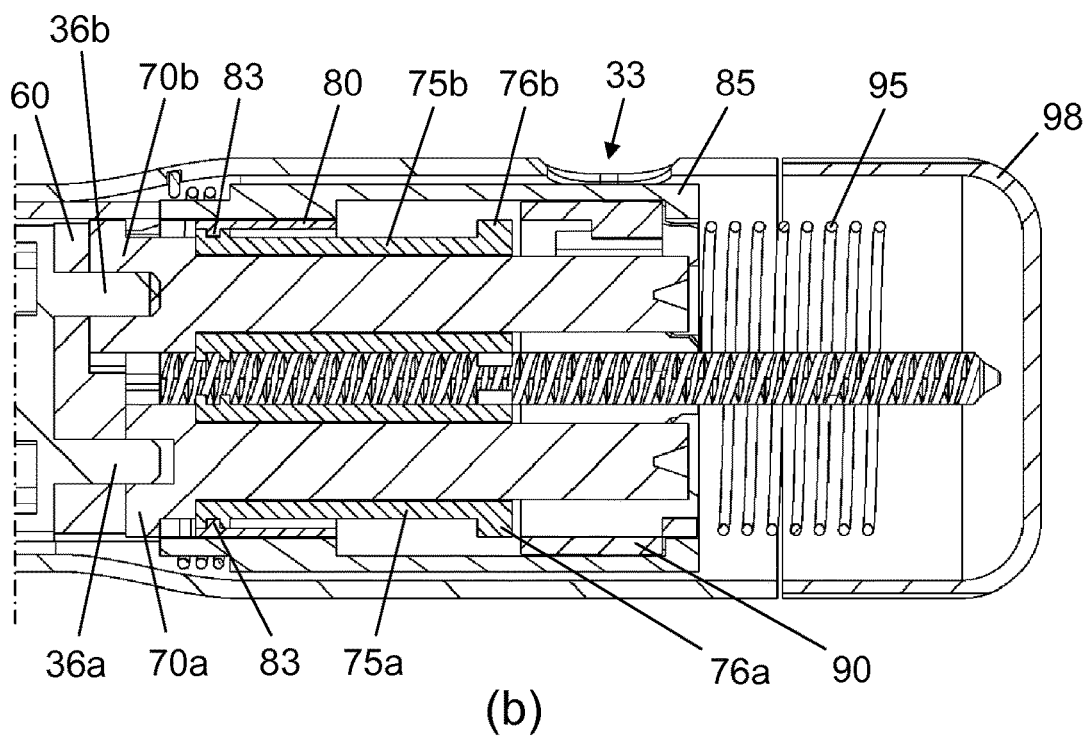
Fig. 4

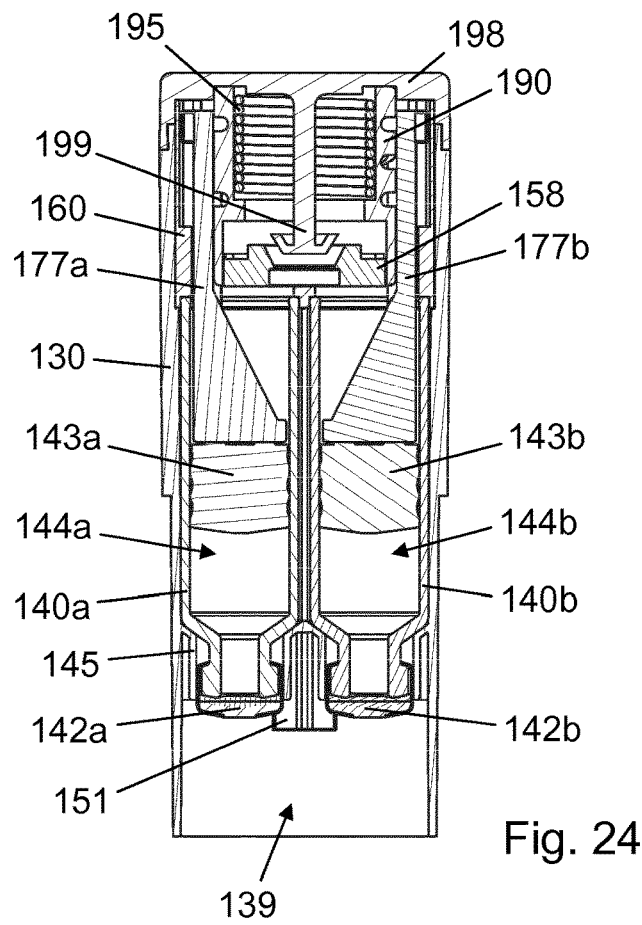
Fig. 24
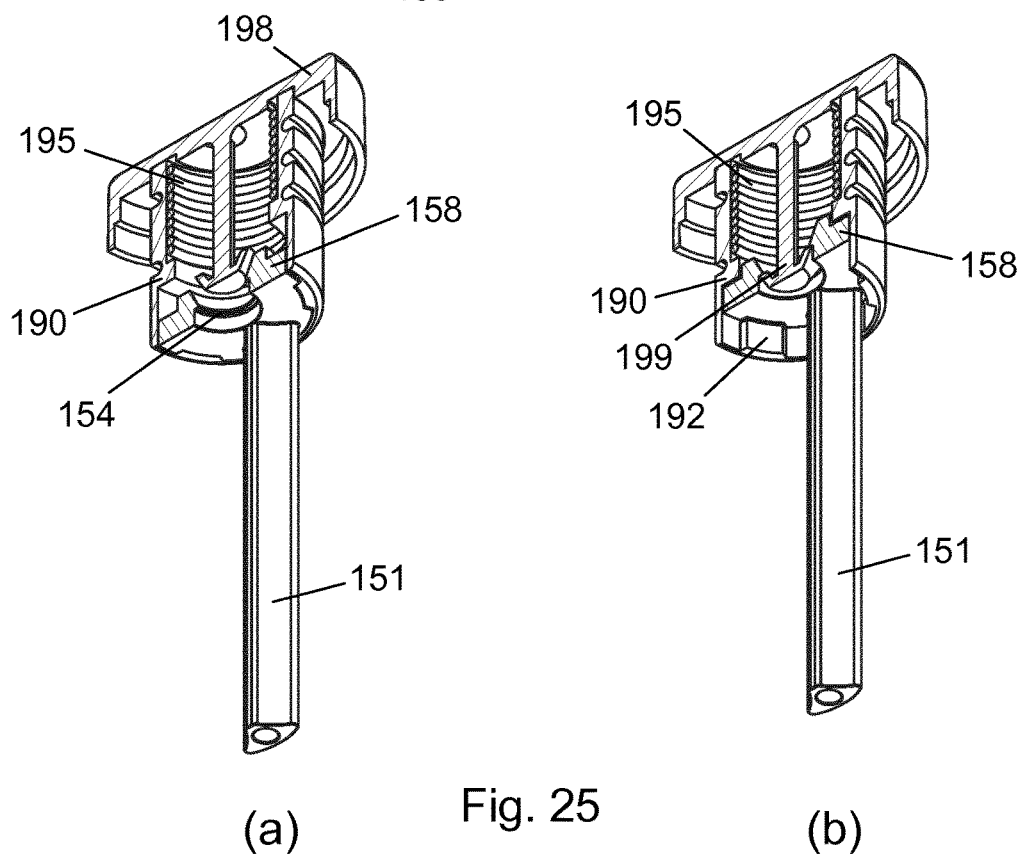
(a) Fig. 25 (b)

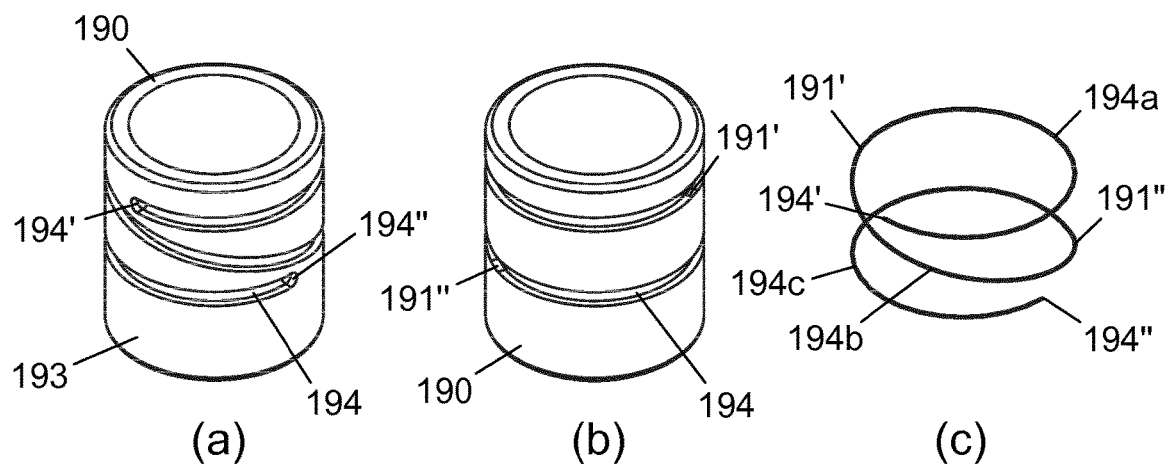
Fig. 26
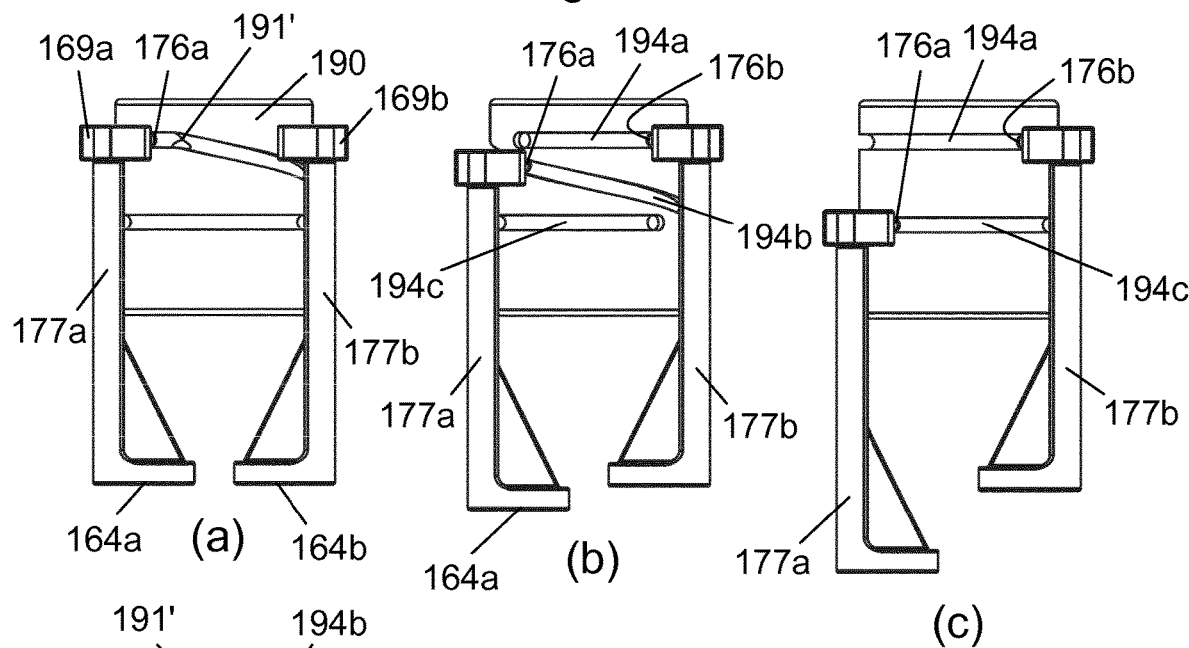
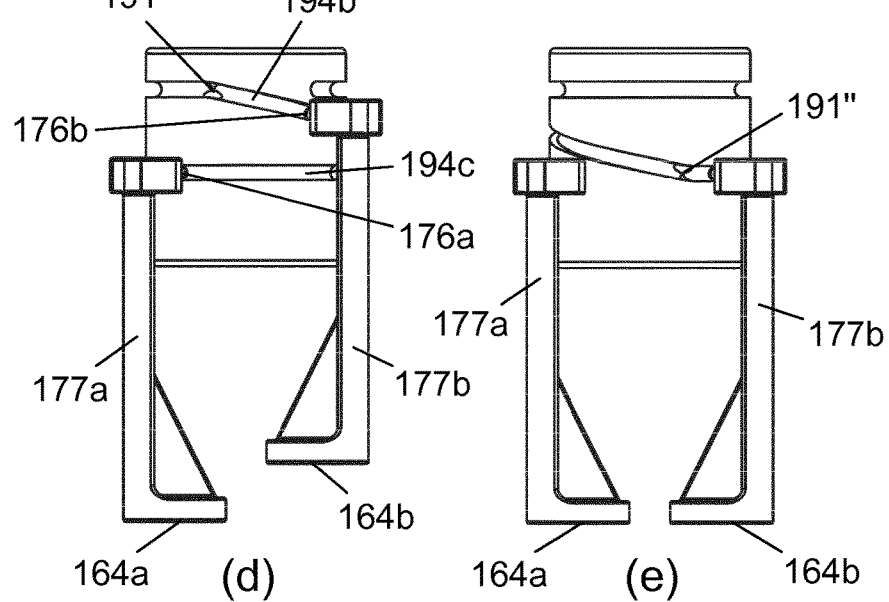
Fig. 27

MECHANISM FOR SEQUENTIAL DOSE DELIVERY

CROSS-REFERENCE TO RELATED APPLICATIONS

This application is a 35 U.S.C. § 371 National Stage application of International Application PCT/EP2016/082875 (published as WO 2017/114921), filed Dec. 29, 2016, which claims priority to European Patent Application 15203071.4, filed Dec. 30, 2015, the contents thereof which are incorporated by reference in their entirety.

FIELD OF THE INVENTION

The present invention relates to drug delivery devices capable of sequential administration of liquid substances, e.g. through a single dispense interface.

BACKGROUND OF THE INVENTION

Within some medical treatment areas a combination therapy involving co-administration of at least two active agents is advantageous because of synergistic or additive effects. For example, within diabetes care, in the management of type 2 diabetes mellitus, concomitant use of certain insulin and glp-1 products has been shown to reduce $HbA_{1c}$ levels in subjects, thereby improving glycaemic control.

Many drugs must be administered parenterally to be effective in the body and some of these, e.g. insulin and glp-1, may require one or more doses to be delivered subcutaneously on a daily basis. Subcutaneous drug delivery is often associated with discomfort as many people dislike the thought of having an injection needle inserted through the skin. An undisclosed number of people even suffer from needle-phobia, and these people have a particularly strong desire to escape multiple daily injection therapy.

One attractive scenario, therefore, is to reduce the number of required skin penetrations by administering the injectable media at the same time, or substantially the same time. In that respect prefabricated mixtures of the involved media are not always an optimal solution. For one, some substances are only stable in mixed form short-term, and it may accordingly be necessary to keep those substances apart until just prior to administration. Adding to that, the individual subject users may have different needs in terms of dose ratios of the constituent active ingredients. Even a single subject user may sometimes require varying dose ratios of the active ingredients in a relatively short time span, e.g. during a titration period. It may thus not be feasible to cover all the individual needs by premixed pharmaceutical products.

In some cases a co-administration of two separate substances through a single dispense interface can yield improved effects if the co-administration is truly sequential, i.e. if it is guaranteed that the one substance is delivered completely before the delivery of the other substance is initiated. Many prior art drug delivery devices capable of such co-administration do not offer a truly sequential delivery of the substances.

WO 2012/072541 (Sanofi-Aventis Deutschland GmbH) discloses a drug delivery device solution which is allegedly capable of sequential drug administration from two cartridges through a single delivery needle. The device is semi-automatic in the sense that the user must manually operate a button to dispense drug from one of the cartridges, after which a spring is released to assist the user in dispensing drug from the other cartridge. During dose setting a dose setter and a dial component move helically out of the body of the device and during dose delivery, in order to dispense drug from the device the dose setter and the dial component move helically back into the body of the device. This helical back and forth movement of the dose setter and the dial component relative to the body of the device adds to the overall use size and handling complexity of the device, which some users may find inconvenient. It is desirable to offer a drug delivery device with a simpler user interface which does not require the user to change hand position during a dose administration procedure in order to accommodate for components moving out of the body of the device.

SUMMARY OF THE INVENTION

It is an object of the invention to eliminate or reduce at least one drawback of the prior art, or to provide a useful alternative to prior art solutions.

In particular, it is an object of the invention to provide a drug delivery device for sequential administration of substances, e.g. through a single dispense interface, which device employs a simple and truly sequential dosing mechanism.

It is a further object of the invention to provide such a drug delivery device which is relatively compact in configuration and which is easy for the user to handle.

It is an even further object of the invention to provide such a drug delivery device which offers a plurality of different user selectable dose sizes.

In the disclosure of the present invention, aspects and embodiments will be described which will address one or more of the above objects and/or which will address objects apparent from the following text.

In one aspect of the invention a drug delivery device according to claim 1 is provided.

Thereby, a drug delivery device for sequential administration of substances is provided, which drug delivery device comprises a first variable volume reservoir holding a first substance and comprising a first outlet and a first displaceable wall, a second variable volume reservoir holding a second substance and comprising a second outlet and a second displaceable wall, a first wall actuation structure activatable to move the first displaceable wall and thereby expel a dose of the first substance through the first outlet, a second wall actuation structure activatable to move the second displaceable wall and thereby expel a dose of the second substance through the second outlet, and a drive structure for actuating the first wall actuation structure and the second wall actuation structure.

The drive structure performs a predetermined movement to execute a sequential administration of the first substance and the second substance. This predetermined movement comprises a first part movement followed by a second part movement. During the first part movement the drive structure drives the first wall actuation structure, while the second wall actuation structure remains stationary, and during the second part movement the drive structure drives the second wall actuation structure, while the first wall actuation structure remains stationary.

Since during the first part movement of the drive structure the second wall actuation structure, and thereby the second displaceable wall, is stationary, and during the second part movement of the drive structure the first wall actuation structure, and thereby the first displaceable wall, is stationary, a truly sequential dosing mechanism is provided which firstly administers the dose of the first substance completely and secondly administers the dose of the second substance completely.

In particular, the predetermined movement of the drive structure which executes the sequential administration of the first substance and the second substance may be uninterrupted, which makes the device suitable for being powered by a spring. The sequential dosing mechanism can thereby be made fully automatic which relieves the user of the manual labour connected with activating the drive structure. In relation to a manual dosing mechanism an uninterrupted movement of the drive structure may ensure that the user does not have to e.g. change grip, force or pace during a dose expelling operation, as it provides for a smooth shift between the actuations of the respective wall actuation structures.

The drug delivery device may further comprise a housing extending along a housing axis and accommodating, at least partly, the first wall actuation structure and the second wall actuation structure, and the drive structure may be axially fixed with respect to the housing axis during the predetermined movement. The drive structure does thereby not move axially relative to the housing at any point during the sequential administration of the first substance and the second substance, enabling a user to maintain the same hold of the device throughout the administration procedure. The predetermined movement is accordingly a predetermined rotation comprising a first part rotation followed by a second part rotation.

In case of an automatic version of the drug delivery device a torsion spring may be operatively coupled with the drive structure and adapted to release stored rotational energy to cause the drive structure to perform the predetermined movement. In particular, the torsion spring may be arranged to act between the drive structure and the housing, or a component which is rotationally fixed with respect to the housing. A release of the torsion spring will thereby cause an actuation of the drive structure through the predetermined movement, e.g. in one uninterrupted stroke, providing a very simple to handle device.

The drive structure may be operatively coupled with the first wall actuation structure and decoupled from the second wall actuation structure during the first part movement and operatively coupled with the second wall actuation structure and decoupled from the first wall actuation structure during the second part movement.

The first wall actuation structure may comprise a first set of teeth and the second wall actuation structure may comprise a second set of teeth, and the drive structure may comprise a plurality of teeth configured for sequential engagement with the first set of teeth and the second set of teeth.

The drive structure may comprise a cylindrical surface and the plurality of teeth may be distributed on the cylindrical surface. It is noted that in this context the term "cylindrical surface" encompasses an annular surface.

The drug delivery device may be configured for one sequential dose administration and subsequent discarding, or it may be configured for multiple sequential dose administrations. For either of these configurations the drug delivery device may offer a single dose or a plurality of user selectable doses. In case of the latter the drive structure may form part of a user operable dose setting mechanism and the extent of the predetermined movement may be selectable by the user in accordance with a predefined dose setting scale. This will allow the user to use the same drug delivery device to administer different doses of the first substance and the second substance, in a fixed ratio, which may e.g. be relevant in a titration phase.

The drive structure may comprise a plurality of dose related indicia and may thereby function as a dose indicator. This may reduce the number of components needed to realise the sequential dosing mechanism.

The drive structure may be axially fixed with respect to the housing axis at all times, i.e. including during a dose setting operation. This provides for a simple to handle drug delivery device being compact both in idle state and in use.

The drive structure may extend along a drive structure axis, and the first wall actuation structure and the second wall actuation structure may be capable of engagement with the drive structure in a number of different axial positions of the first set of teeth and the second set of teeth relative to the cylindrical surface. The number of different axial positions may correspond to the number of settable doses on the predefined dose setting scale.

In each of the number of different axial positions the first set of teeth and the second set of teeth may be adapted to sequentially engage with a dose specific number of the plurality of teeth on the drive structure.

In particular embodiments of the invention the cylindrical surface is an inner surface oriented radially inwardly, and the first set of teeth and the second set of teeth are axially displaceable within a space surrounded by the inner surface. This enables the provision of a relatively compact sequential dosing mechanism.

In other embodiments of the invention the cylindrical surface is an outer surface oriented radially outwardly.

The plurality of teeth may be arranged such that during one sequential administration of the first substance and the second substance a first engaging tooth will engage with the second set of teeth immediately after a last engaging tooth disengages from the first set of teeth. This will prevent the drive structure from gaining momentum as it moves from a state in which it is engaged with the first set of teeth to a state in which it is engaged with the second set of teeth. Such a gained momentum could lead to an unpleasant jerk in the device as the drive structure suddenly impacted the second set of teeth at a great speed.

The term "immediately after" should be understood such that the unloaded movement of the drive structure between disengagement from the first set of teeth to engagement with the second set of teeth is no more than twice the length of the loaded movement which the drive structure undergoes as one single of the plurality of teeth engages with and subsequently disengages from the first set of teeth.

In an alternative embodiment of the invention the drive structure comprises a cylindrical exterior surface provided with guide means, which guide means comprises a first guide track for guiding the first wall actuation structure and a second guide track for guiding the second wall actuation structure. The first wall actuation structure is rotationally locked with respect to the housing and comprises a first track follower being slidably engaged with the first guide track, and the second wall actuation structure is rotationally locked with respect to the housing and comprises a second track follower being slidably engaged with the second guide track.

The first guide track comprises a partly helical first guide track portion and a partly circular first guide track portion in extension thereof, and the second guide track comprises a partly circular second guide track portion and a partly helical second guide track portion in extension thereof. The predetermined movement is a predetermined rotation comprising a first part rotation followed by a second part rotation. The first track follower is adapted to travel the partly helical first guide track portion during the first part rotation and the partly circular first guide track portion during the second part rotation, and the second track follower is adapted to travel the partly circular second guide track portion during the first part rotation and the partly helical second guide track portion during the second part rotation.

This ensures that in the course of the predetermined movement of the drive structure the first wall actuation structure and the second wall actuation structure are activated sequentially and hence that the first wall actuation structure completes its axial movement in the housing before the second wall actuation structure commences any axial movement.

In special cases the partly helical first guide track portion and the partly helical second guide track portion coincide such that the first guide track and the second guide track form a single continuous track. This enables a shorter drive structure, providing for an even more compact drug delivery device.

The first variable volume reservoir and the second variable volume reservoir may be physically separate entities, i.e. individually manufactured self-contained structures, which may be identical, or at least substantially identical. For example, the first variable volume reservoir may be a first cartridge comprising a first cartridge body, a first self-sealing penetrable septum and a first slidable piston, and the second variable volume reservoir may be a second cartridge comprising a second cartridge body, a second self-sealing penetrable septum and a second slidable piston. As one alternative, the first variable volume reservoir may be a first syringe comprising a first syringe barrel and a first slidable piston, and the second variable volume reservoir may be a second syringe comprising a second syringe barrel and a second slidable piston. In either case the first wall actuation structure may be or comprise a first piston rod, and the second wall actuation structure may be or comprise a second piston rod. In certain embodiments of the invention, the first variable volume reservoir and the second variable volume reservoir are arranged side-by-side.

The first outlet may be fluidly connected with, or adapted to be fluidly connected with, a first hollow needle and the second outlet may be fluidly connected with, or adapted to be fluidly connected with, a second hollow needle. The first hollow needle and the second hollow needle may be adapted for penetration of a human skin barrier, such that the first substance is delivered directly from the first variable volume reservoir through the first hollow needle into a first injection site, and the second substance is delivered directly from the second variable volume reservoir through the second hollow needle into a second injection site.

Alternatively, the first hollow needle and the second hollow needle may both be fluidly connected with a single dispense interface, such as a third hollow needle adapted for penetration of a human skin barrier, e.g. in a manifold type of construction. Thereby, both the first substance and the second substance are delivered through the third hollow needle. This solution is particularly attractive for users who are reluctant to needle insertions.

It is noted that the particular way of conveying the first substance and the second substance from the respective first and second variable volume reservoirs to the human body is irrelevant to the present invention which is only concerned with the order of expelling of the first substance and the second substance from, respectively, the first variable volume reservoir and the second variable volume reservoir. In that connection, to underline the above, it is emphasized that, as a further alternative, at least one of the first outlet and the second outlet could comprise a jet nozzle, and that at least one of the first substance and the second substance thereby could be administered to the body by needle-free jet injection.

Although believed to be implicitly clear, in order to avoid any confusion it is emphasized that the terms "axial" and "axially" when used in a context of the housing refer to the housing axis and when used in a context of the drive structure refer to the drive structure axis. The housing axis and the drive structure axis are longitudinal axes which may coincide.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein FIG. 2 is a longitudinal section view of a drug delivery device forming part of the drug delivery system, FIG. 3 shows two longitudinal section views of a needle module for use with the drug delivery device, FIG. 4 shows two close-up sectional views of a proximal portion of the drug delivery device, FIG. 24 is a longitudinal section view of the drug delivery device of FIG. 22, FIG. 25 shows the release mechanism for the drug delivery device in two different states, FIG. 26 shows the drum and the track sections used to drive the piston rods sequentially, and FIG. 27 show side views of the drum and the piston rods in different states during drug expelling.

In the figures like structures are mainly identified by like reference numerals.

DESCRIPTION OF EXEMPLARY EMBODIMENTS

When in the following relative expressions, such as "upper" and "lower", are used, these refer to the appended figures and not necessarily to an actual situation of use. The shown figures are schematic representations for which reason the configuration of the different structures as well as their relative dimensions are intended to serve illustrative purposes only.

Figure 1:
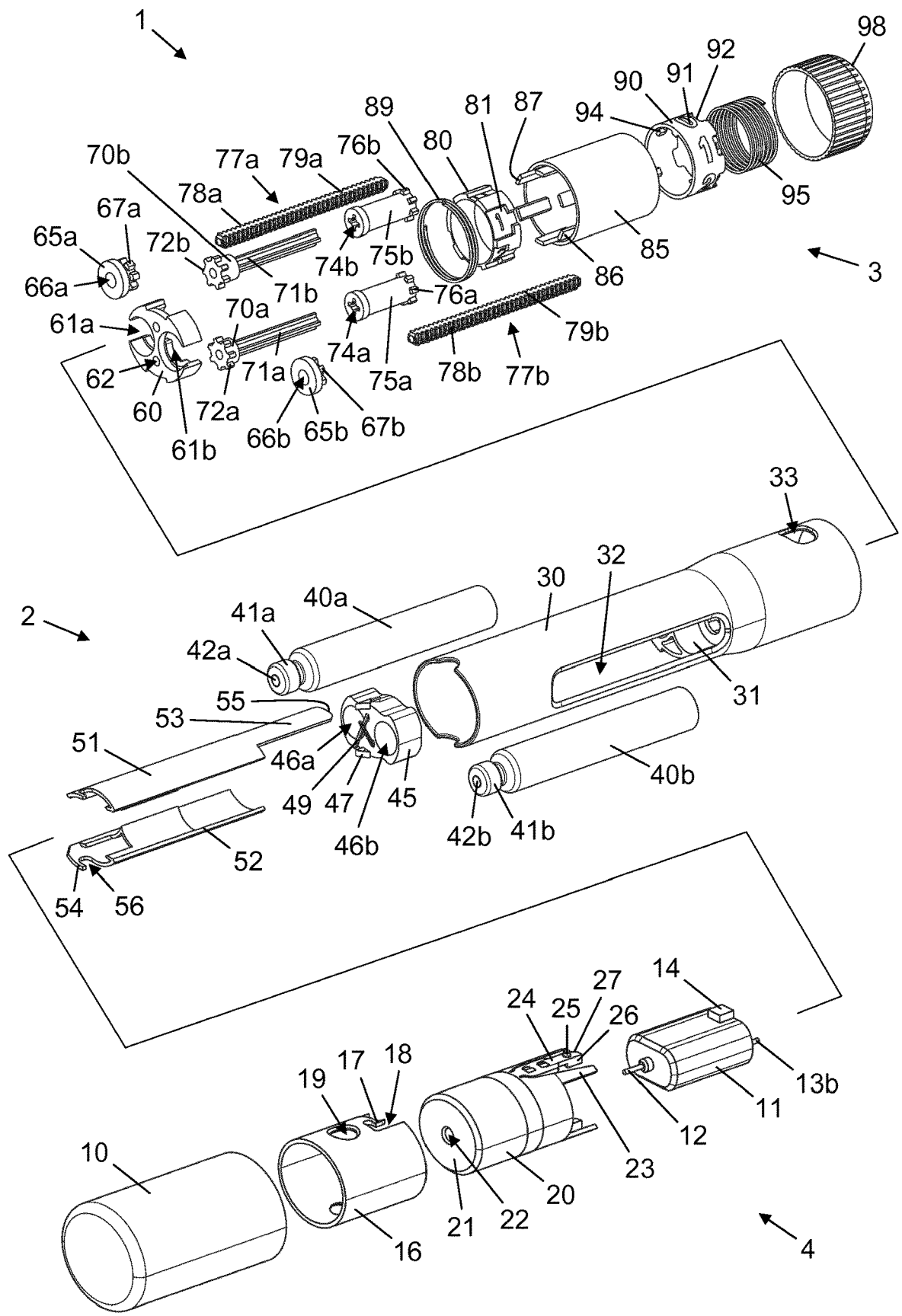
FIG. 1 is an exploded view of a drug delivery system according to an embodiment of the invention.

FIG. 1 is an exploded view of a drug delivery system 1 according to an exemplary embodiment of the invention. The drug delivery system 1 comprises a drug delivery device 2, 3 to be used with a separate needle module 4. The drug delivery device 2, 3 comprises a device housing structure 2 and a dose engine 3.

The device housing structure 2 comprises a main body 30 adapted to accommodate a first cartridge 40a holding a first substance, a second cartridge 40b holding a second substance, as well as a portion of the dose engine 3. The needle module 4 is a single use unit which is attachable to a distal end portion of the device housing structure 2 and which can be used for effecting one sequential administration of the first substance and the second substance.

The main body 30 extends along a longitudinal axis and is provided with an elongated central window 32 allowing for inspection of the respective cartridge contents, and a small dose window 33 at a proximal end portion for verification of a set dose. Just proximally of the elongated central window 32 a bulkhead 31 separates a cartridge accommodating portion of the main body 30 from a dose engine accommodating portion.

Axially and rotationally fixed within the main body is a cartridge chassis 45, serving to retain the first cartridge 40a and the second cartridge 40b in predefined positions against the bulkhead 31. The cartridge chassis 45 has a first cartridge receiving bore 46a adapted to envelop an outlet end portion 41a of the first cartridge 40a and a second cartridge receiving bore 46a adapted to envelop an outlet end portion 41b of the second cartridge 40b. On a distal end face the cartridge chassis 45 carries a pair of chassis chamfers 47 and a chassis spring 49, the respective purposes of which will be explained below.

A first shield transfer element 51 and a diametrically opposite second shield transfer element 52 extend longitudinally within the main body 30. The first shield transfer element 51 comprises a transfer leg 53 which extends through the bulkhead 31 and into the dose engine accommodating portion, the bulkhead 31 thereby rotationally fixing the first shield transfer element 51 with respect to the main body 30. The transfer leg 53 has a proximally oriented abutment surface 55 for interaction with parts of the dose engine 3, as explained further below. Both shield transfer elements 51, 52 have a distal retaining hook 54, the arrangement of which defining respective receiving spaces 56.

The needle module 4 comprises a needle hub 11 having a front needle 12 for penetration of human skin, a first back needle 13a (not visible) adapted to penetrate a first self-sealing septum 42a closing the outlet end portion 41a of the first cartridge 40a, and a second back needle 13b adapted to penetrate a second self-sealing septum 42b closing the outlet end portion 41b of the first cartridge 40b. Both back needles 13a, 13b are fluidly connected with the front needle 12 such that the first substance may be transferred from the first cartridge 40a through the first back needle 13a and the front needle 12 to a desired, e.g. subcutaneous, delivery site, and the second substance may be transferred from the second cartridge 40b through the second back needle 13b and the front needle 12 to the same delivery site.

The needle hub 11 is slidably received in a needle shield 20 such that in a non-active state of the needle module 4 the front needle 12 is positioned behind an end wall 21, thereby eliminating any risks of accidental needle pricking. However, during use, in an active state of the needle module 4, the front needle 12 protrudes from a bore 22 in the end wall 21. The needle hub 11 is biased proximally, i.e. away from the end wall 21, by a needle return spring 29 (see FIG. 3) in the needle shield 20.

The needle shield 20 has a number of proximally extending legs 23 as well as a pair of diametrically opposite radially and laterally deflectable arms 24. Each arm 24 carries a guide pin 25, a proximal thickened portion 26, and a shield chamfer 27, the latter being adapted for cooperation with a respective one of the chassis chamfers 47 following a finalised dose administration, and the thickened portion 26 being adapted for cooperation with a raised surface 14 on the needle hub 11 when the needle shield 20 and the needle hub 11 are in a certain relative axial position.

A needle housing 16 accommodates a portion of the needle shield 20 and serves to position the needle module 4 properly on the device housing structure 2 as well as to prevent reuse of a used needle module 4. To the effect of the latter the needle housing 16 is provided with a finger 17 at a proximal end portion, the finger 17 defining a bayonet track 18 adapted to receive the guide pin 25 in a manner which will be described further below. A pair of diametrically opposite openings 19 allow for user manipulation of the arms 24 to dismount the needle module 4 from the device housing structure 2. Notably, this is only possible before the front needle 12 is caused to protrude from the bore 22.

Before use of the needle module 4 the needle hub 11, the needle shield 20, and the needle housing 16 are accommodated in an outer cap 10 which is sealed by a removable sterile barrier in the form of a peel-off foil 15 (see FIG. 3).

The dose engine 3 comprises a gear chassis 60 having two holes 62 through which respective stub shafts 36a, 36b (see FIG. 4b) on the proximal side of the bulkhead 31 extend. The gear chassis 60 further has a first bearing 61a for a first piston rod guide 65a and a second bearing 61b for a second piston rod guide 65b. The first piston rod guide 61a has a threaded pass-through 66a and a toothed rim 67a, while the second piston rod guide 61b has a threaded pass-through 66b and a toothed rim 67b. The toothed rims 67a, 67b are axially offset from one another.

A first piston rod 77a having an interrupted thread 78a along its entire length and an axially extending smooth surface 79a is configured for reception in the pass-through 66a. Similarly, a second piston rod 77b having an interrupted thread 78b along its entire length and an axially extending smooth surface 79b is configured for reception in the pass-through 66b. The two piston rods 77a, 77b are thus arranged in parallel, and they extend through respective first and second through holes 35a, 35b (see FIG. 10) in the bulkhead 31. The first through hole 35a has a flattened cross-section to prevent relative rotational motion between the first piston rod 77a and the main body 30. Similarly, the second through hole 35b has a flattened cross-section to prevent relative rotational motion between the second piston rod 77b and the main body 30.

Also arranged in parallel but at right angles to the two piston rods 77a, 77b are a first lay shaft 70a and a second lay shaft 70b. The first lay shaft 70a comprises a cruciform shaft portion 71a, on which a first top gear 75a having a corresponding cruciform bore 74a is slidably mounted, and a toothed rim 72a. The second lay shaft 70b comprises a cruciform shaft portion 71b, on which a first top gear 75b having a corresponding cruciform bore 74b is slidably mounted, and a toothed rim 72b. The toothed rims 72a, 72b are axially offset from one another, such that the toothed rim 72a on the first lay shaft 70a is aligned with the toothed rim 67a on the first piston rod guide 65a and the toothed rim 72b on the second lay shaft 70b is aligned with the toothed rim 67b on the second piston rod guide 65b. Thereby, the first lay shaft 70a is rotationally coupled with the first piston rod guide 65a and the second lay shaft 70b is rotationally coupled with the second piston rod guide 65b.

An axially slidable and rotatable annular dose locator 80 is arranged about the two piston rods 77a, 77b and the two lay shafts 70a, 70b. The dose locator 80 is axially fixed to the two top gears 75a, 75b and is provided with a plurality of differently sized pockets 81 configured to receive the transfer leg 53 of the first shield transfer element 51.

The dose locator 80 is surrounded by a transparent cylindrical scale connector 85 having a plurality of splines 86 which extend distally through respective longitudinal tracks 82 (see FIG. 11a) in the dose locator 80, thereby rotationally fixing the dose locator 80 to the scale connector 85. Each of the splines 86 has an abutment surface 87 for interaction with the abutment surface 55 on the transfer leg 53. The scale connector 85 is translationally and rotationally biased by a dose locator return spring 89, as described further below.

A scale drum 90 carrying a plurality of dose related ciphers 91 is arranged within the scale connector 85, proximally of the dose locator 80. At its proximal rim the scale drum 90 is provided with a plurality of indents 92. In a dose setting state of the drug delivery device 2, 3 the scale drum 90 is rotationally fixed to the scale connector 85 via these indents 92 and mating radial protrusions 88 (see FIG. 4a) on an interior surface of the scale connector 85, and a dose can be set by rotation of a dose dial 98.

A plurality of radially inwardly protruding teeth 94 are provided on the scale drum 90 in a specific pattern which will be explained in detail below. The teeth 94 are arranged to mesh with, respectively, a toothed rim 76a on the first top gear 75a and a toothed rim 76b on the second top gear 75b during a sequential dose administration. The dosing mechanism is powered by a torsion spring 95 in a manner generally known from automatic injection pens used in the diabetes care segment and may be released automatically, e.g. in response to the first shield transfer element 51 reaching a particular axial position in the main body 30, or manually by the user operating a dedicated dose release button (not shown).

FIG. 2 is a longitudinal section view of the drug delivery device 2, 3 before attachment of the needle module 4. It shows the two cartridges 40a, 40b arranged side by side with the respective self-sealing septa 42a, 42b pointing downwards. The first cartridge 40a is sealed at its upper end by an axially slidable piston 43a which together with the first self-sealing septum 42a and the cartridge wall defines a first chamber 44a in which the first substance is contained. Similarly, the second cartridge 40b is sealed at its upper end by an axially slidable piston 43b which together with the second self-sealing septum 42b and the cartridge wall defines a second chamber 44b in which the second substance is contained.

FIG. 3a is a longitudinal section view of the needle module 4 in a pre-use state in which the needle hub 11 is aseptically housed in a sealed space defined by the outer cap 10 and the peel-off foil 15. The needle return spring 29 is a compression spring acting between the needle hub 11 and the needle shield 20.

FIG. 3b is a sectional view of the needle module 4 along line b-b of FIG. 3a. It can be seen that the relative positions of the needle hub 11, the needle shield 20, and the needle housing 16 in this configuration of the needle module 4 allows for a radially inwards deflection of the arms 24 in response to a user pressing e.g. a thumb and a forefinger through the respective openings 19, following removal of the outer cap 10.

FIG. 4a is a close-up view of a proximal portion of the drug delivery device 2, 3 indicated by section Q in FIG. 2, displaying the various elements of the dose engine 3 in more detail. The drug delivery device 3 is in the dose setting state where a rotation of the dose dial 98 leads to a rotational positioning of the scale drum 90 in accordance with the desired dose size and a corresponding rotation of both the scale connector 85, due to the engagement between the radial protrusions 88 and the indents 92, and the dose locator 80, due to the presence of the splines 86 in the longitudinal tracks 82.

FIG. 4b is a sectional view of the proximal portion of the drug delivery device 2, 3 along line b-b of FIG. 4a. Notably, in this view a circular interior protrusion 83 on the dose locator 80 is visible, which interior protrusion 83 is used to axially fix the dose locator 80 to both the first top gear 75a and the second top gear 75b. Also, it can be seen that in the dose setting state of the drug delivery device 2, 3 the toothed rims 76a, 76b are disconnected from the scale drum 90.

Figure 5:
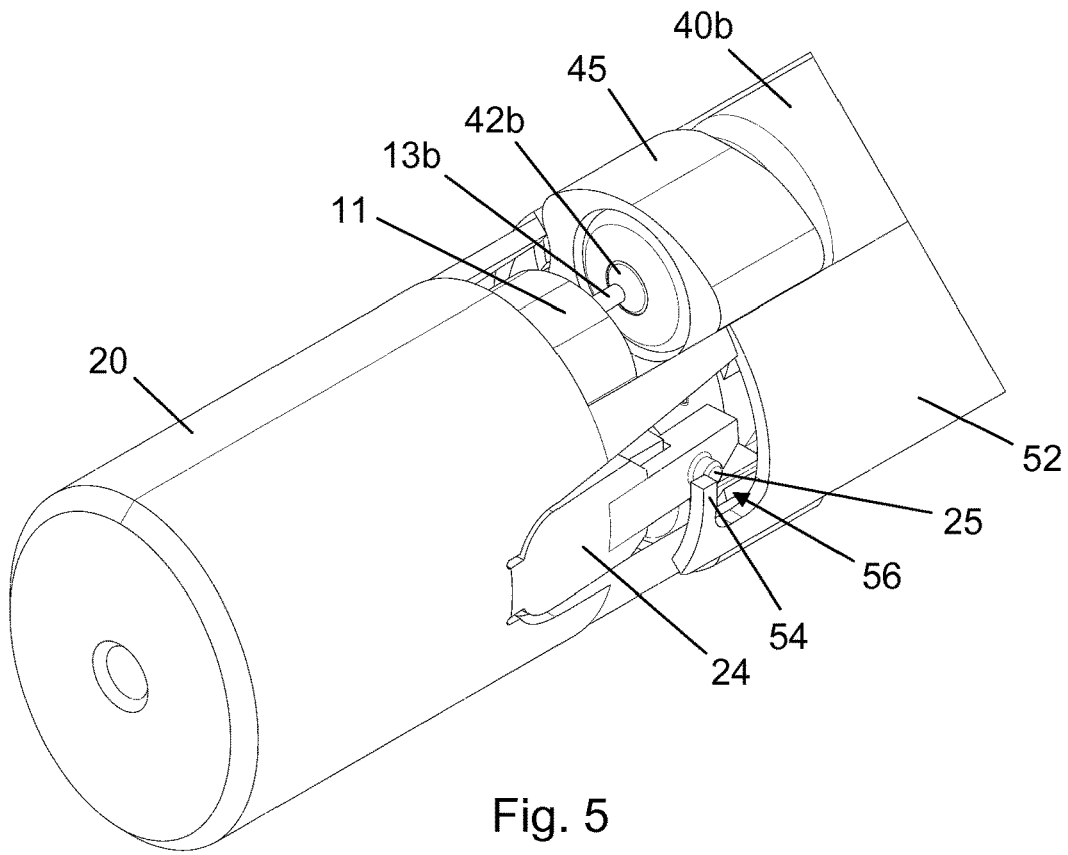
FIGS. 5 and 6 show a perspective view of parts of the needle module during mounting, respectively after mounting, of the needle module onto the drug delivery device.

FIG. 5 is a perspective view of parts of the needle module 4 during attachment to the drug delivery device 2, 3. For the sake of clarity the needle housing 16 and the outer cap 10 have been omitted. The figure specifically shows how one of the arms 24 deflect radially inwardly, either prompted automatically during the converging relative axial motion between the needle shield 20 and the main body 30 by the interaction between dedicated geometries or caused by the user's compression through the opening 19, to allow the guide pin 25 to pass the retaining hook 54 and snap into the receiving space 56.

Figure 6:
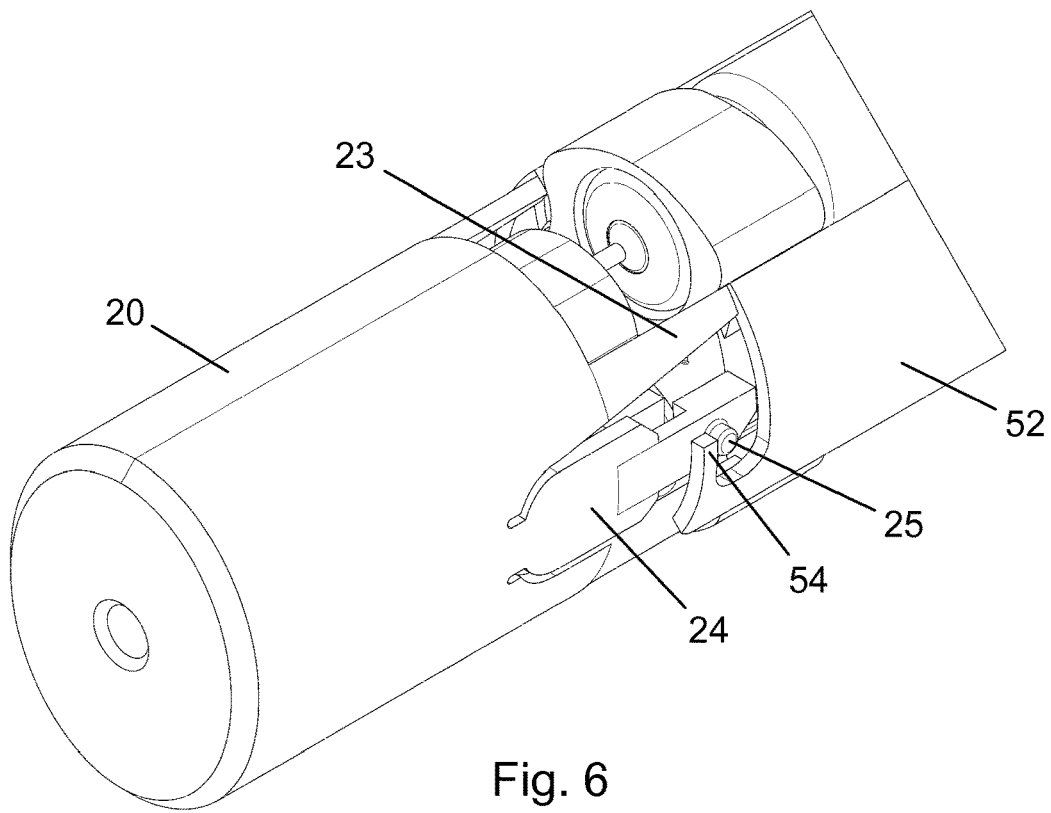

In FIG. 6 the guide pin 25 is securely positioned in the receiving space 56 and the leg 23 abuts the second shield transfer element 52. On the opposite side of the needle hub 11 a similar connection has taken place between the other guide pin 25 and the first shield transfer element 51. Thereby, the needle shield 20 has become axially locked to the shield transfer elements 51, 52. Notably, in this attached state of the needle module 4 the back needles 13a, 13b have not yet penetrated the septa 42a, 42b, and the needle module 4 may therefore be removed from the drug delivery device 2, 3 simply by the user applying a compressive force through the openings 19 to depress the arms 24 and subsequently pulling the needle shield 20 axially away from the main body 30.

Figure 7:
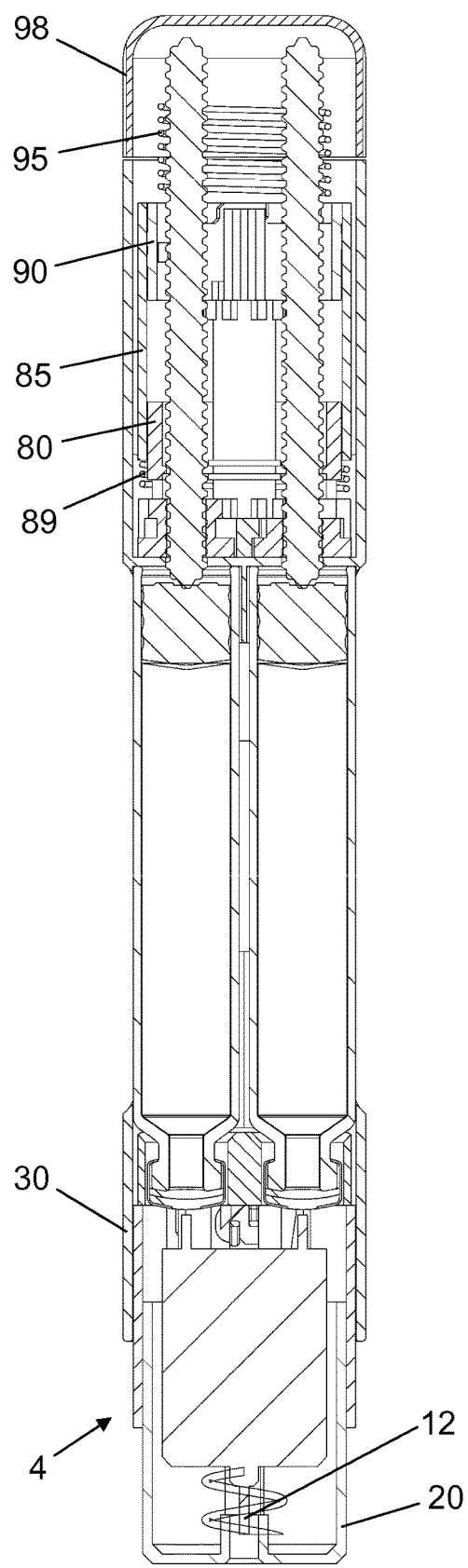
FIGS. 7-10 show longitudinal section views of the drug delivery system in various states during expelling of a dose of drug.

FIG. 7 is a longitudinal section view of the drug delivery system 1 in the attached state of the needle module 4, corresponding to FIG. 6, with the outer cap 10 removed. At this point a desired dose to be delivered is set by rotation of the dose dial 98. The rotation of the dose dial 98 results in an angular positioning of the scale drum 90 relative to the main body 30 as well as a torsional straining of the power spring 95. The power spring 95 is maintained in the strained state by a releasable ratchet mechanism (not shown). The dose ciphers 91 are successively viewable through the dose window 33 as the scale drum 90 is turned, and each offered dose size is associated with a unique angular position of the scale drum 90. Due to the rotational relationship between the scale drum 90 and the scale connector 85 and between the scale connector 85 and the dose locator 80, both the scale connector 85 and the dose locator 80 are angularly displaced relative to the main body 30 corresponding to the angular displacement of the scale drum 90, and the dose locator return spring 89, being arranged to act between the scale connector 85 and the main body 30, is torsionally strained, thereby providing a biasing torque to the scale connector 85 and the dose locator 80. The dose locator return spring 89 is maintained in the strained state by a releasable ratchet mechanism (not shown).

When a desired dose is set the drug delivery system 1 is ready to deliver a certain volume of the first substance followed by a certain volume of the second substance by release of the power spring 95. The particular volumes delivered are dictated by the chosen dose in accordance with the specific construction of the drug delivery device 2, 3.

Figure 8:
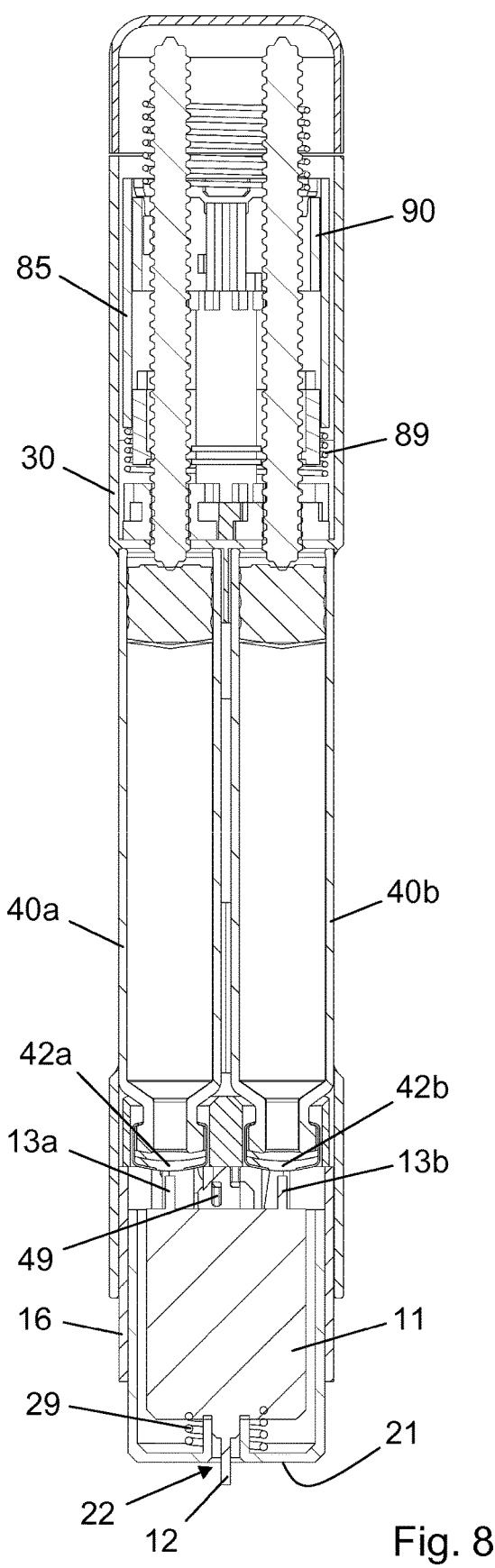

To administer the set dose the user places the end wall 21 on the skin at a desired injection site and presses the drug delivery system 1 against the skin. The chassis spring 49 is stiffer than the needle return spring 29, so firstly the needle return spring 29 will be compressed as the needle shield 20 slides on the outside of the needle hub 11, leading to a protrusion of the front needle 12 from the bore 22 and thereby an insertion of the front needle 12 into the skin. This is depicted in FIG. 8.

As the needle shield 20 moves proximally relative to the main body 30 the shield transfer elements 51, 52 move, accordingly, proximally relative to the bulkhead 31, whereby the abutment surface 55 applies a pushing force to the abutment surface 87, axially displacing the scale connector 85 and lifting the radial protrusions 88 out of engagement with the indents 92. The scale connector 85 is thereby rotationally disengaged from the scale drum 90. The proximal displacement of the scale connector 85 leads to a stretching of the dose locator return spring 89. The dose locator return spring 89 thus biases the scale connector 85, and thereby the shield transfer elements 51, 52 and the needle shield 20, distally relative to the main body 30.

Figure 9:
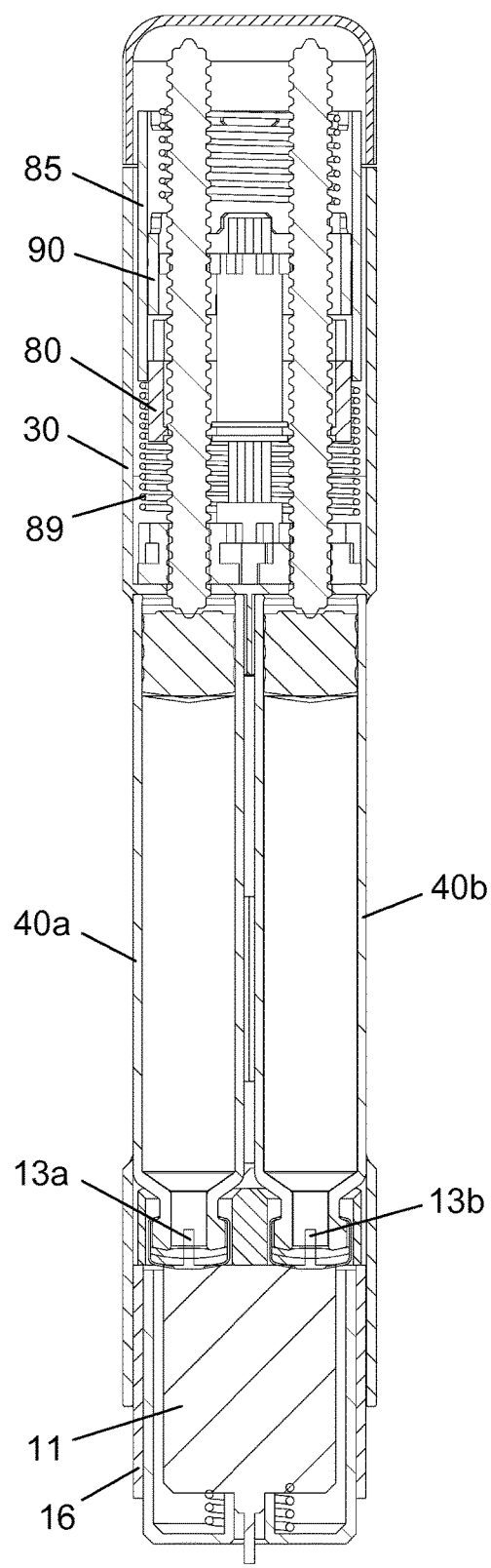

Subsequent to the above mentioned the pressing of the drug delivery system 1 against the skin will lead to a compression of the chassis spring 49 and a simultaneous penetration of the first septum 42a by the first back needle 13a and of the second septum 42b by the second back needle 13b as the needle hub 11 slides within the main body 30 in unison with the needle shield 20. This is depicted in FIG. 9. Fluid communication is thereby established between the first back needle 13a and the interior of the first cartridge 40a and between the second back needle 13b and the interior of the second cartridge 40b, and the needle module 4 is now in a connected state.

The additional proximal movement of the needle shield 20 leads to a further proximal movement of the shield transfer elements 51, 52, which causes the transfer leg 53 to enter into a dose specific pocket 81 and the abutment surface 55, resultantly, to axially displace the dose locator 80 relative to the main body 30. Since the abutment surface 55 still abuts the abutment surface 87 of one of the splines 86 the scale connector 85 is displaced a corresponding distance in the main body 30, further straining the dose locator return spring 89 axially.

Due to the axial fixation of the top gears 75a, 75b to the dose locator 80 via the interior protrusion 83 the aforementioned displacement of the dose locator 80 brings the toothed rims 76a, 76b into engagement with the teeth 94 on the scale drum 90. As the scale connector 85 reaches a specific point the power spring 95 is released, and the scale drum 90 is urged to rotate back to its initial angular position in the main body 30, thereby successively activating the first lay shaft 70a and the second lay shaft 70b, leading to a sequential administration of the first substance and the second substance. The dose specific positioning of the toothed rims 76a, 76b within the annular space defined by the scale drum 90 as well as the dose administration resulting from the return of the scale drum 90 are described further below in connection with FIGS. 11-19.

Figure 10:
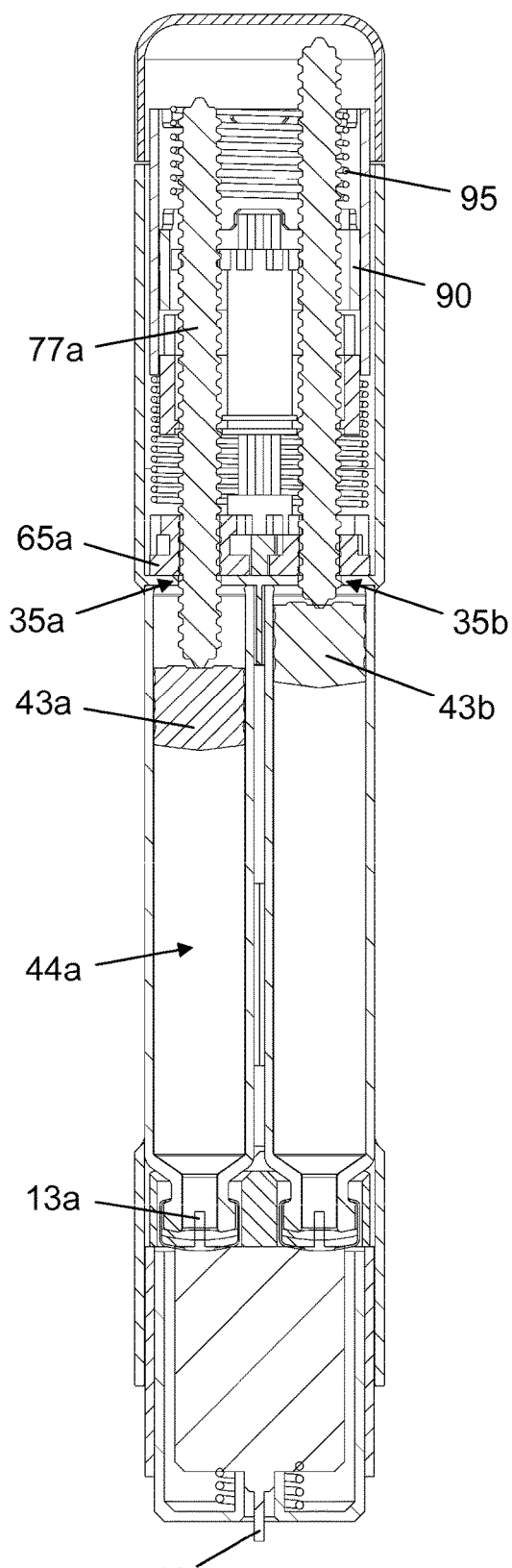

FIG. 10 shows the drug delivery system 1 in a state where the scale drum 90 has travelled exactly half of the angular distance towards its initial position. It is seen that only the first piston rod guide 65a has been activated at this point, leading to an advancement of the first piston rod 77a through the first through hole 35a, and that the second piston rod 77b has remained motionless relative to the second through hole 35b. Accordingly, the first piston 43a has been displaced in the first cartridge 40a and expelled the dose of the first substance from the first chamber 44a through the first back needle 13a and the front needle 12, while the second piston 43b is still in the full cartridge position. As the power spring 95 continues to lead the scale drum 90 back the first piston rod 77a will become motionless while the second piston rod 77b will be activated as a consequence of the second piston rod guide 65b being rotated. The delivery sequence will be clear from the below description.

In the present embodiment the drug delivery device 2, 3 offers five different doses, "dose 1"-"dose 5". As mentioned previously the dose is selected by the user by rotating the dose dial 98, and the rotation of the dose dial 98 leads to corresponding rotations of the scale drum 90 and the dose locator 80. The angular position of the dose locator in the main body 30 is therefore uniquely coupled to the selected dose.

FIGS. 11-14 sketch the dose delivery mechanism in four different stages, in combined perspective and sectional views, during delivery of "dose 3". For the sake of clarity elements such as the main body 30, the scale connector 85, and the dose locator return spring 89 are omitted from the views. Further, to enhance the visibility of the components within the annular space defined by the scale drum 90 the proximal half of the scale drum 90 has been cut away in the perspective views.

Figure 11:
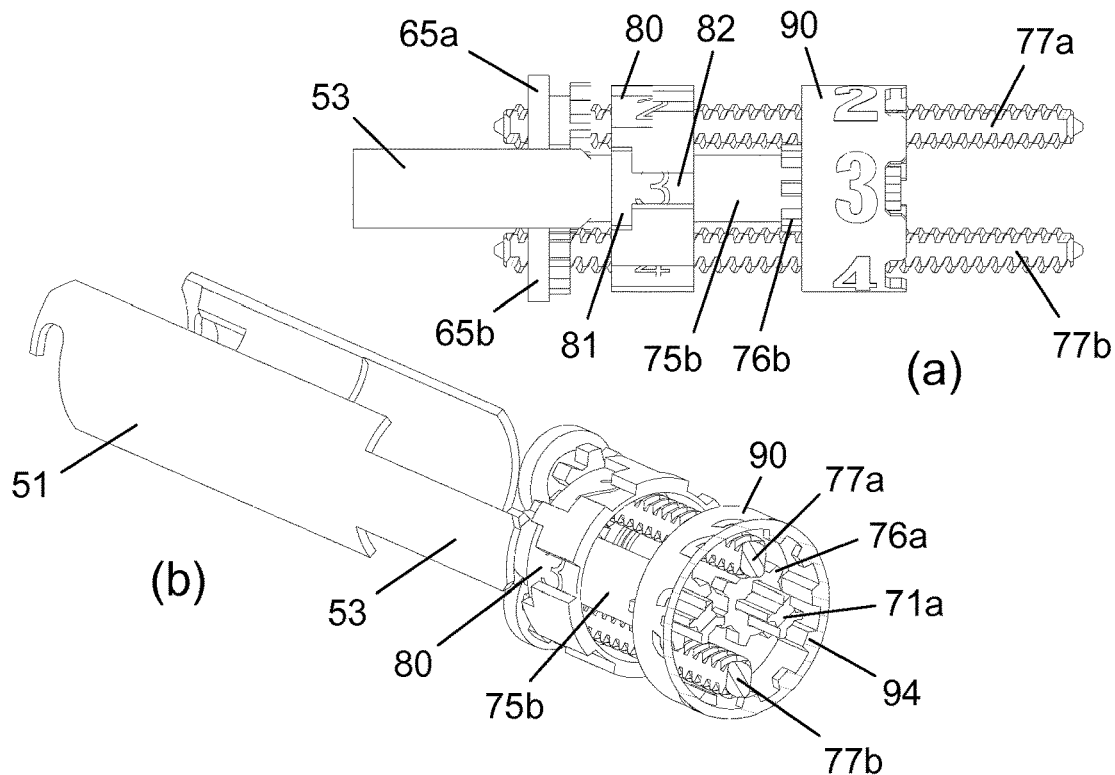
FIGS. 11-14 show different views of a dosing mechanism in the drug delivery device during one sequential substance administration.

FIG. 11 shows that following the setting of "dose 3" the scale drum 90 and the dose locator 80 are angularly aligned at "3". The proximal displacement of the first shield transfer element 51, and thereby of the transfer leg 53, relative to the main body 30 is predetermined and independent of the set dose. The shield transfer elements 51, 52 are axially locked to the needle shield 20 which is displaced the same distance proximally relative to the main body 30 every time the front needle 12 is positioned in the skin and the back needles 13a, 13b are pushed through the septa 42a, 42b. Hence, the transfer leg 53 is always displaced the same distance in response to the front needle 12 and the back needles 13a, 13b being inserted, regardless of the selected dose. However, the angular position of the dose locator 80 varies, and the respective depths of the pockets 81 correspond to respective doses such that the abutment surface 55 will interact with a pocket wall at varying axial positions, depending on the selected dose. This means that for five possible doses the dose locator 80 is displaced five different distances axially in response to the front needle 12 and the back needles 13a, 13b being inserted, and that the actual displacement of the dose locator 80 is specific to a particular dose.

The view in FIG. 11 corresponds to the attached state of the needle module 4 shown in FIG. 7, where the back needles 13a, 13b have not yet penetrated the septa 42a, 42b. It is seen that the transfer leg 53 has not yet entered into the specific pocket 81 pertaining to "dose 3" and that the toothed rims 76a, 76b are out of engagement with the teeth 94.

Figure 12:
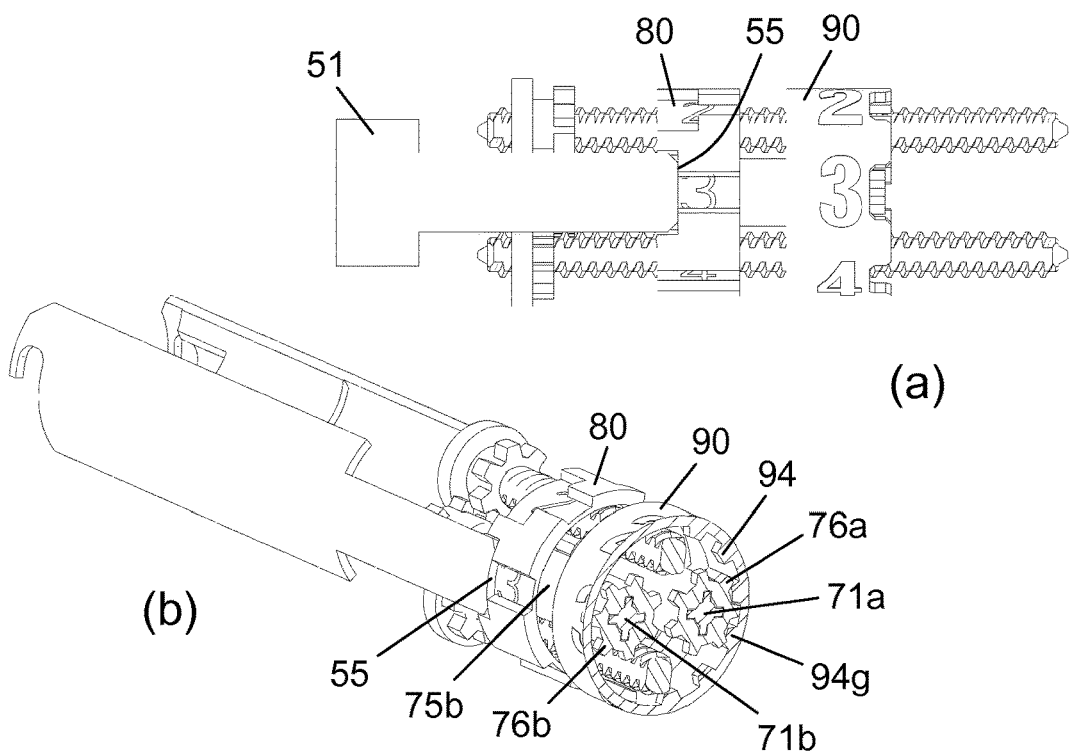

The view in FIG. 12 corresponds to the connected state of the needle module 4 shown in FIG. 9. At this point the transfer leg 53 has entered into the pocket 81 and the abutment surface 55 has forced the dose locator 80 to displace axially towards the scale drum 90 a particular distance dictated by the depth of the pocket 81. As the dose locator 80 moves axially the top gears 75a, 75b slide correspondingly along the cruciform shaft portions 71a, 71b of the respective lay shafts 70a, 70b, and the axial displacement of the toothed rims 76a, 76b is accordingly strictly correlated with the selected dose. The teeth 94 on the interior surface of the scale drum 90 are distributed in five different axial layers corresponding to the five selectable doses, "dose 1"-"dose 5", and the toothed rims 76a, 76b will interact differently with the teeth 94 in the five different axial layers, as described below in connection with FIGS. 15-19.

FIG. 12b shows how the axial displacement of the dose locator 80 has caused the toothed rims 76a, 76b to become positioned within the scale drum 90 at the "dose 3" layer of teeth 94 in which a first meshing tooth 94g is ready to engage with the toothed rim 76a and consequently rotate the first top gear 75a.

Figure 13:
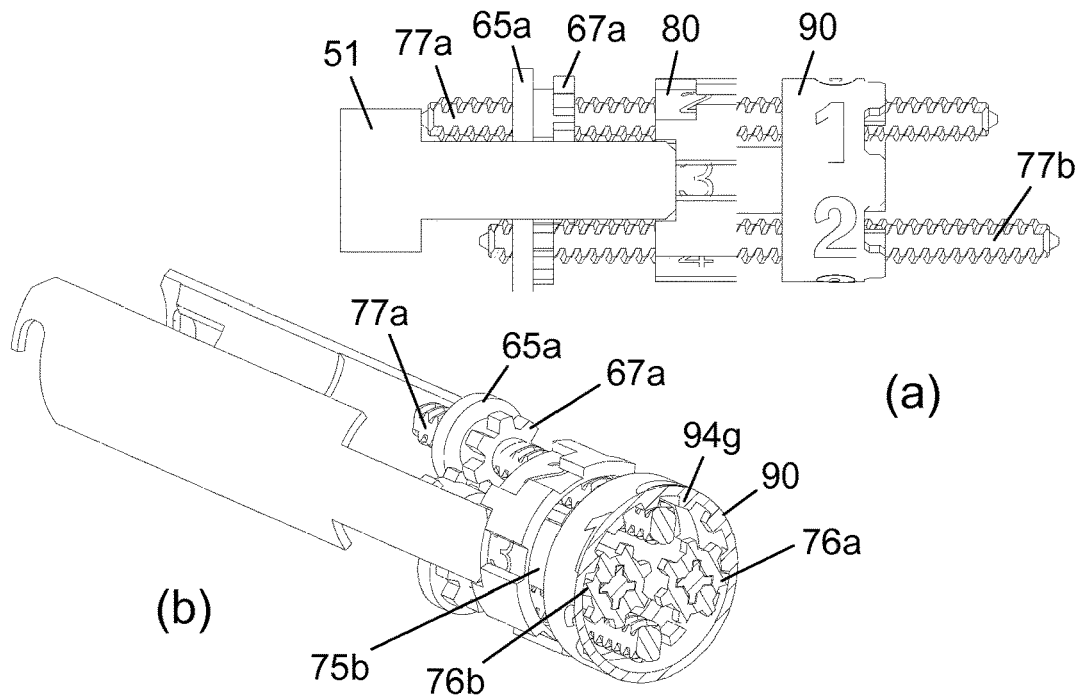

The view in FIG. 13 corresponds to the half-completed dose view of FIG. 10. The scale drum 90 has been rotated by the torsionally relaxing power spring 95 and has undergone exactly half of the angular displacement from its dose setting position. This has caused the first meshing tooth 94g and two immediately succeeding teeth to rotate the first top gear 75a which due to the rotational engagement between the toothed head 72a and the toothed rim 67a in turn has rotated the first piston rod guide 65a. The threaded interface between the pass-through 66a and the first piston rod 77a and the splined connection of the first piston rod 77a to the bulkhead 31 has consequently caused the first piston rod 77a to advance axially a dose specific distance. This is best seen in FIG. 13a.

The teeth 94 are now in a position where further rotation of the scale drum 90 will cause interaction with the toothed rim 76b and thereby rotation of the second top gear 75b. This can be seen from FIG. 13b. Notably, since the scale drum 90 and the scale connector 85 are rotationally decoupled and since the dose locator 80 is rotationally locked to the transfer leg 53, the scale drum 90 rotates relative to the dose locator 80 during this part of the dose administration.

Figure 14:
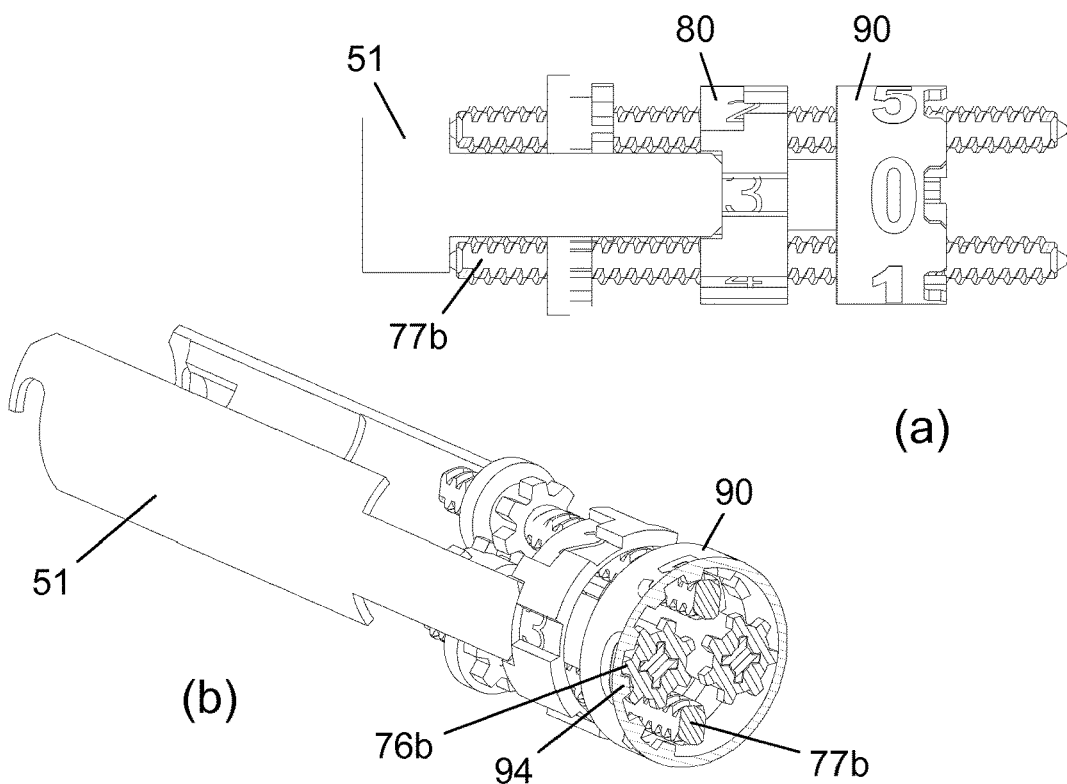

In FIG. 14 the scale drum 90 has undergone the second half of the rotation back to its initial position which has caused an axial advancement of the second piston rod 77b in response to three teeth 94 having consecutively meshed with the toothed rim 76b. The advancement of the second piston rod 77b is best seen in FIG. 14a, while FIG. 14b best illustrates the movement of the three teeth 94 in question, when compared to FIG. 13b.

So, while the dose setting action serves to angularly position the scale drum 90 relative to the main body 30, the needle module connecting action serves to, apart from establish a required flow path from the cartridges 40a, 40b to the body, axially position the top gears 75a, 75b relative to the angularly positioned scale drum 90. These two actions together ensure that a volume of the first substance and a volume of the second substance are administered sequentially in accordance with the set dose, as the power spring 95 subsequently releases a portion of its stored energy. It is noted that the respective administered volumes of the first substance and the second substance may be identical or may be different, depending on the specific construction of the drug delivery device 2, 3 chosen by the manufacturer. For example, the first interrupted thread 78a and the second interrupted thread 78b may have different pitches, whereby identical angular displacements of the first top gear 75a and the second top gear 75b will lead to different axial displacements of the first piston rod 77a and the second piston rod 77b and thereby of the first piston 43a and the second piston 43b.

FIGS. 15-19 show top views of the scale drum 90, the first top gear 75a, the second top gear 75b, the first piston rod 77a, and the second piston rod 77b in five different cross-sections of the scale drum 90, corresponding to the aforementioned five axial layers. For the sake of clarity, each cross-sectional view shows only the configuration of teeth 94 that are active in the corresponding axial layer. Each view shows the components in a state where a dose of the first substance has been administered from the drug delivery system 1 and where an administration of a dose of the second substance is about to commence.

Figure 15:
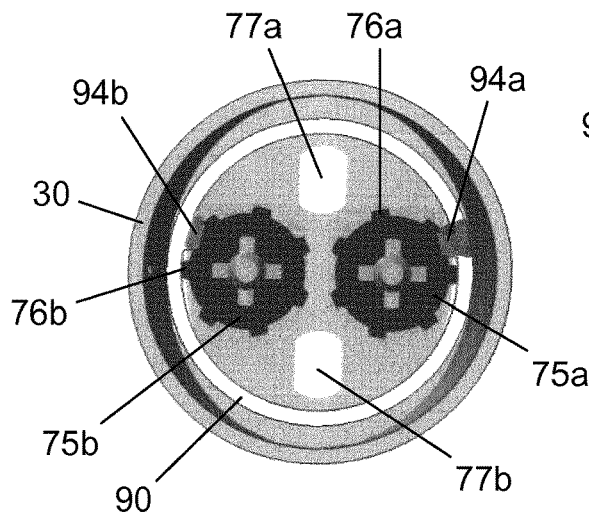
FIGS. 15-19 show cross-sectional top views of the drive structure engagement for five different dose sizes.

FIG. 15 is a cross-sectional view through the "dose 1" layer of the scale drum 90. For the present embodiment of the invention the toothed rims 76a, 76b reach this layer by the shortest axial travel of the dose locator 80 caused by the displacement of the transfer leg 53, since by the angular positioning of the dose locator 80 corresponding to a set dose of size "dose 1" the transfer leg 53 becomes aligned with the deepest of the pockets 81. As can be seen from the figure two teeth 94a, 94b are present in this layer. The teeth 94a, 94b are arranged such that when a dose of size "dose 1" is set and the needle module 4 is in the connected state the tooth 94a will be positioned adjacent to, and ready to engage with, a tooth on the toothed rim 76a of the first top gear 75a, while the tooth 94b will be positioned a short distance away from the toothed rim 76b of the second top gear 75b.

As the scale drum 90 rotates back to its initial, "0", position in response to the release of the power spring 95 first the tooth 94a engages with the toothed rim 76a and rotates the first top gear 75a while the tooth 94b approaches the toothed rim 76b, then the tooth 94a disengages from the toothed rim 76a just as the tooth 94b reaches the toothed rim 76b. This is the state shown in FIG. 15. At this point the first top gear 75a has been rotated "x" degrees leading to a corresponding rotation of the first piston rod guide 65a due to the rotational interlocked relationship between the first top gear 75a and the first lay shaft 70a and the rotational engagement between the toothed head 72a and the toothed rim 67a. The rotation of the first piston rod guide 65a by "x" degrees has led to a distal displacement of the first piston rod 77a, and thereby of the first piston 43a, the magnitude of the displacement being determined by the pitch of the threaded connection between the interrupted thread 78a and the pass-through 66a. Consequently, a volume of the first substance has been expelled from the first chamber 44a through the first back needle 13a and the front needle 12.

The continued rotation of the scale drum 90 now leads the tooth 94b to engage with the toothed rim 76b and rotate the second top gear 75b "x" degrees, while the tooth 94a moves freely along a part-circular path. Thereby, the second piston rod 77b is activated to expel a dose of the second substance from the second chamber 44b through the second back needle 13b and the front needle 12, similarly to the above described expelling of the first substance, while the first piston rod 77a remains stationary. A true sequential administration of the first substance and the second substance is thus realised in response to an angular displacement of the scale drum 90. Notably, the angular displacement of the scale drum 90 needed to administer "dose 1" is less than 360°.

Figure 16:
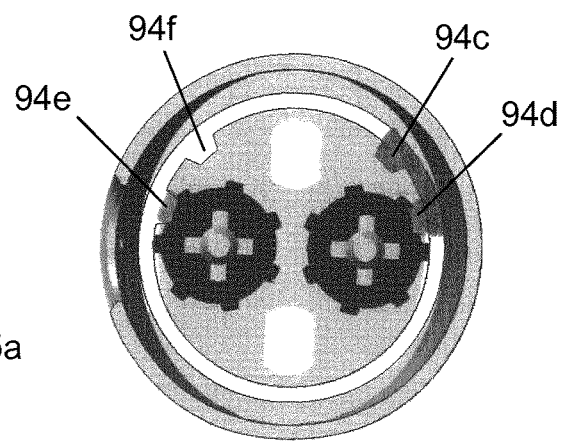

FIG. 16 is a cross-sectional view through the "dose 2" layer of the scale drum 90. In this layer four teeth 94c, 94d, 94e, 94f are distributed along the inner circumference of the scale drum 90. The teeth 94c, 94d are dedicated to interact with the toothed rim 76a of the first top gear 75a, while the teeth 94e, 94f are dedicated to interact with the toothed rim 76b of the second top gear 75b. In this case the teeth 94c, 94d have both engaged with and disengaged from the toothed rim 76a before the teeth 94e, 94f move into engagement with the toothed rim 76b, thereby securing the sequential administration. Since two teeth 94 interact with each toothed rim 76a, 76b the respective top gears 75a, 75b are rotated more during administration of "dose 2" than during administration of "dose 1", and the respective piston rods 77a, 77b are accordingly advanced a longer distance distally to expel a larger volume of the first substance, respectively the second substance.

Figure 17:
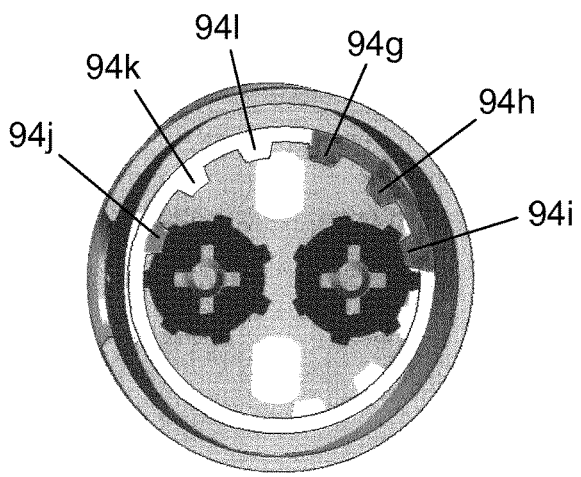

FIG. 17 is a cross-sectional view through the "dose 3" layer of the scale drum 90. This is the layer shown in FIGS. 11-14. In this layer six teeth 94g, 94h, 94i, 94j, 94k, 94l are distributed along the inner circumference of the scale drum 90. Three of the teeth 94g, 94h, 94i are dedicated to interact with the toothed rim 76a of the first top gear 75a, and the other three teeth 94j, 94k, 94l are dedicated to interact with the toothed rim 76b of the second top gear 75b. The state shown in FIG. 17 corresponds to the state shown in FIG. 13b. The first meshing tooth 94g has firstly interacted with the toothed rim 76a, followed by the teeth 94h, 94i. As the tooth 94i disengages from the toothed rim 76a the tooth 94j reaches the toothed rim 76b and the remaining rotation of the scale drum 90 causes the teeth 94j, 94k, 94l to consecutively engage with the toothed rim 76b and rotate the second top gear 75b.

Figure 18:
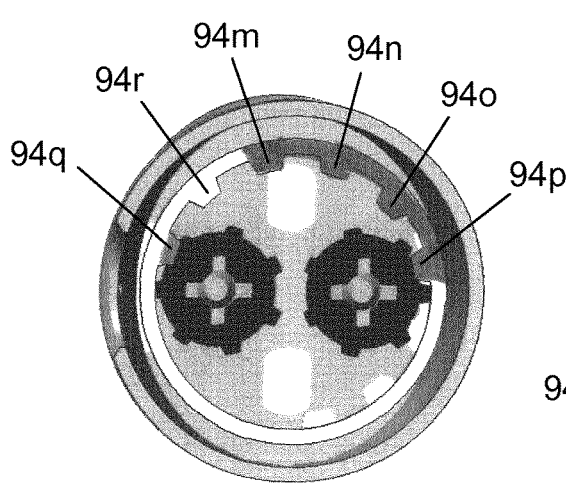

FIG. 18 is a cross-sectional view through the "dose 4" layer of the scale drum 90. This layer also has six active teeth 94m, 94n, 94o, 94p, 94q, 94r, but unlike the previous layers in this layer two teeth 94m, 94n are shared in the sense that they are used to both interact with the toothed rim 76a of the first top gear 75a and with the toothed rim 76b of the second top gear 75b. This way, four teeth 94m, 94n, 94o, 94p are used to rotate the first top gear 75a and four teeth 94q, 94r, 94m, 94n are used to rotate the second top gear 75b.

Figure 19:
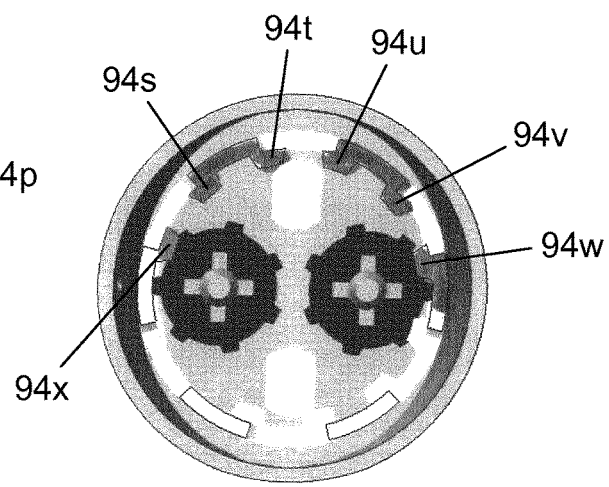

FIG. 19 is a cross-sectional view through the "dose 5" layer of the scale drum 90. Also in this layer six teeth 94s, 94t, 94u, 94v, 94w, 94x are present, but here four teeth 94s, 94t, 94u, 94v are shared such that five teeth 94s, 94t, 94u, 94v, 94w are used to rotate the first top gear 75a and five teeth 94t, 94u, 94v, 94w, 94x are used to rotate the second top gear 75b. Thereby, to administer "dose 5" the scale drum 90 performs almost one complete revolution with respect to the main body 30.

The particular arrangement of the teeth 94 in the various axial layers of the scale drum 90 ensure that once a last interacting tooth leaves the toothed rim 76a of the first top gear 75a a first interacting tooth is about to enter into engagement with the toothed rim 76b of the second top gear 75b. Thereby, a smooth transition between the administration of the first substance and the second substance is guaranteed in the sense that the scale drum 90 will not be able to rotate very long without a tooth being in engagement with one of the toothed rims 76a, 76b. If the teeth 94 were not arranged in this manner the scale drum 90 would be able to gain momentum during movement between interaction with the respective toothed rims 76a, 76b, induced by the torque applying power spring 95, and this could potentially lead to an impact with the toothed rim 76b of the second top gear 75b which would be unpleasant to the user.

Figure 20:
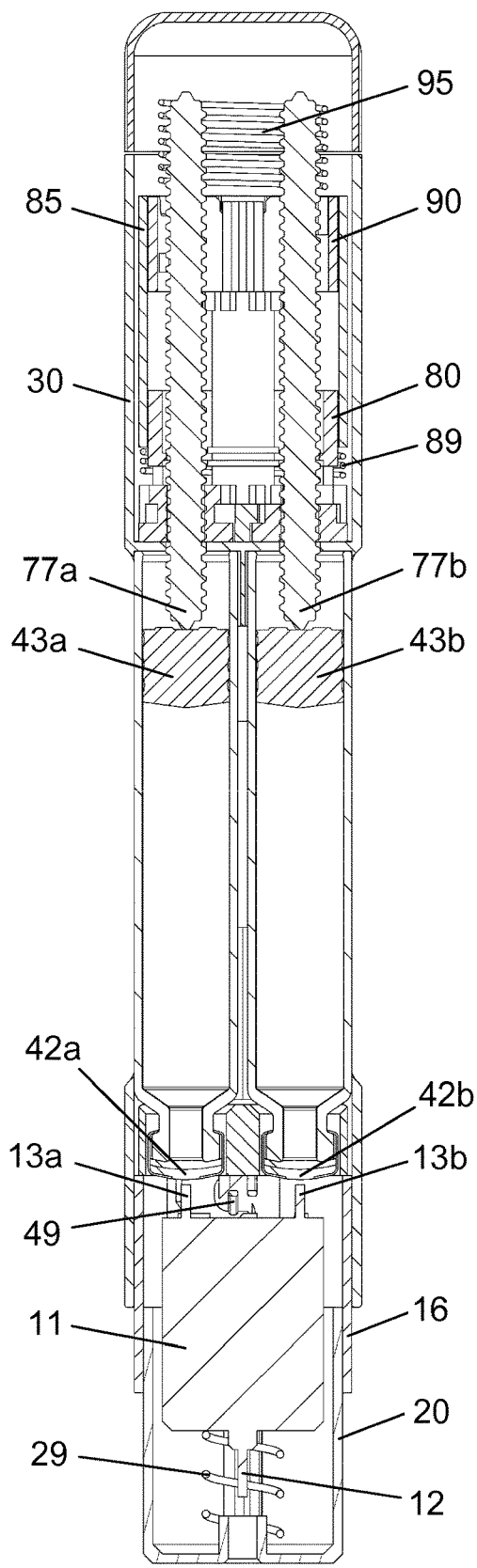
FIG. 20 is a longitudinal section view of the drug delivery system following a sequential dose administration.

FIG. 20 is a longitudinal section view of the drug delivery system 1 after completion of a dose administration and retraction of the front needle 12 from the skin. The first piston 43a and the second piston 43b have been displaced distally the same distance by the respective piston rods 77a, 77b, so the administered volume of the first substance and the administered volume of the second substance is the same.

During retraction of the front needle 12 from the skin because the chassis spring 49 is stiffer than the needle return spring 29 the back needles 13a, 13b are pulled out of the respective septa 42a, 42b before the front needle 12 actually leaves the body. This is important to minimise the risk of contaminating the remaining contents of the respective cartridges 40a, 40b. As the chassis spring 49 causes an axial motion of the needle hub 11 and the needle shield 20 relative to the main body 30 the shield transfer elements 51, 52 are displaced distally in the main body 30. The transfer leg 30 is thereby moved out of the pocket 81, allowing the dose locator return spring 89 to release and automatically rotate the dose locator 80 back to its initial angular position in the main body 30, the "0" dose alignment with the scale drum 90. Furthermore, the dose locator return spring 89 also returns the scale connector 85, and with that the dose locator 80, to their respective initial axial positions in the main body 30. The axial return movement of the dose locator 80 brings the toothed rims 76a, 76b out of the annular space defined by the scale drum 90 and thereby disengages the top gears 75a, 75b from the scale drum 90. The axial return movement of the scale connector 85 leads to a reengagement of the radial protrusions 88 with the indents 92, whereby the scale connector 85 is once again rotationally locked to the scale drum 90.

Figure 21:
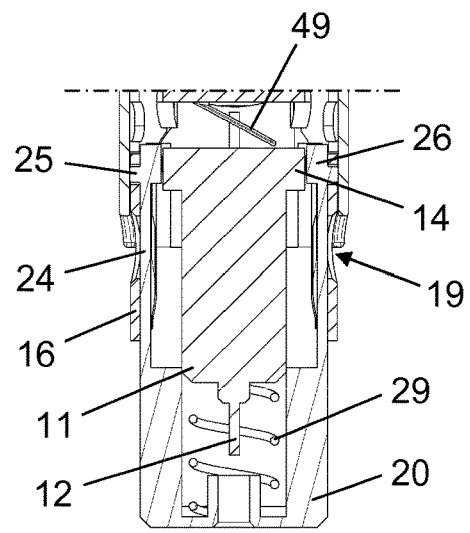
FIG. 21 is a longitudinal section view of the needle module in a locked out state.

FIG. 21 is a longitudinal section view of the needle module 4 in the state shown in FIG. 20. The section view corresponds to the section view shown in FIG. 3b. It can be seen that the needle shield 20 is further advanced by the needle return spring 29 in this state than in the pre-use state shown in FIG. 3b. This is obtained by use of a type of spring driven return mechanism commonly used in ball-pens to retract the marking point into the pen body. In the present case the extension of the needle shield 20 relative to the front needle 12 causes an alignment of the respective thickened portions 26 with the respective raised surfaces 14. This alignment prevents a radial deflection of the arms 24 by depression through the openings 19, thereby ensuring a radial immobilisation of the guide pins 25 which effectively prevents the needle module 4 from being reused, as will be clear from the following.

Figure 22:
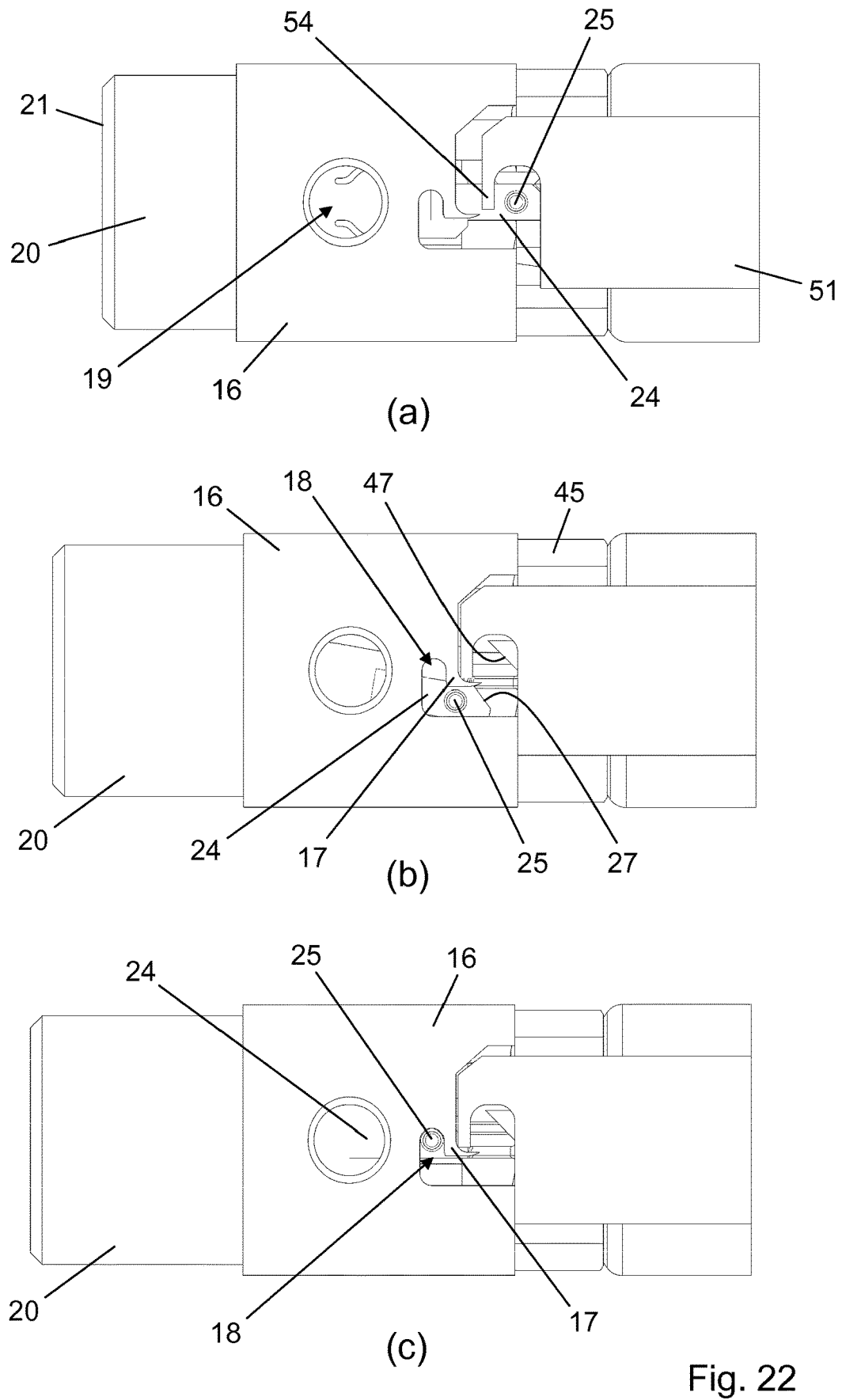
FIG. 22 shows the mechanism for locking out the needle module.

FIG. 22 illustrates the mechanism which prevents the needle module 4 from being used again after a completed dose administration. In FIG. 22a the guide pin 25 is positioned in the receiving space 56 behind the retaining hook 54. As the arm 24 begins to move axially relative to the first transfer shield 51 due to the needle return spring 29 advancing the needle shield 20 relative to the needle housing 16 the shield chamfer 27 slides along the chassis chamfer 47 and thereby causes a lateral deflection of the arm 24. This lateral deflection leads the guide pin 25 around the retaining hook 54 and the finger 17 and into the bayonet track 18, as seen in FIG. 22b.

As the axial movement of the needle shield 20 continues the guide pin 25 passes the finger 17 and the arm 24 pivots back to the non-deflected position, causing the guide pin 25 to move to the bottom of the bayonet track 18, as shown in FIG. 22c. The guide pin 25 is now securely positioned in the bayonet track 18 between the finger 17 and the main structure of the needle housing 16, and the needle shield 20 is thereby axially locked to the needle housing 16 in the extended position in which the front needle 12 is fully covered. Because the guide pin 25 is also radially immobilised, as described above, it is not possible for the user to expose the front needle 12 without damaging the needle module 4. A reuse of the needle module 4 is thereby prevented, which is important in order to reduce the risk of skin reactions as well as contamination and/or cross-contamination of the remaining contents of the cartridges 40a, 40b.

Figure 23:
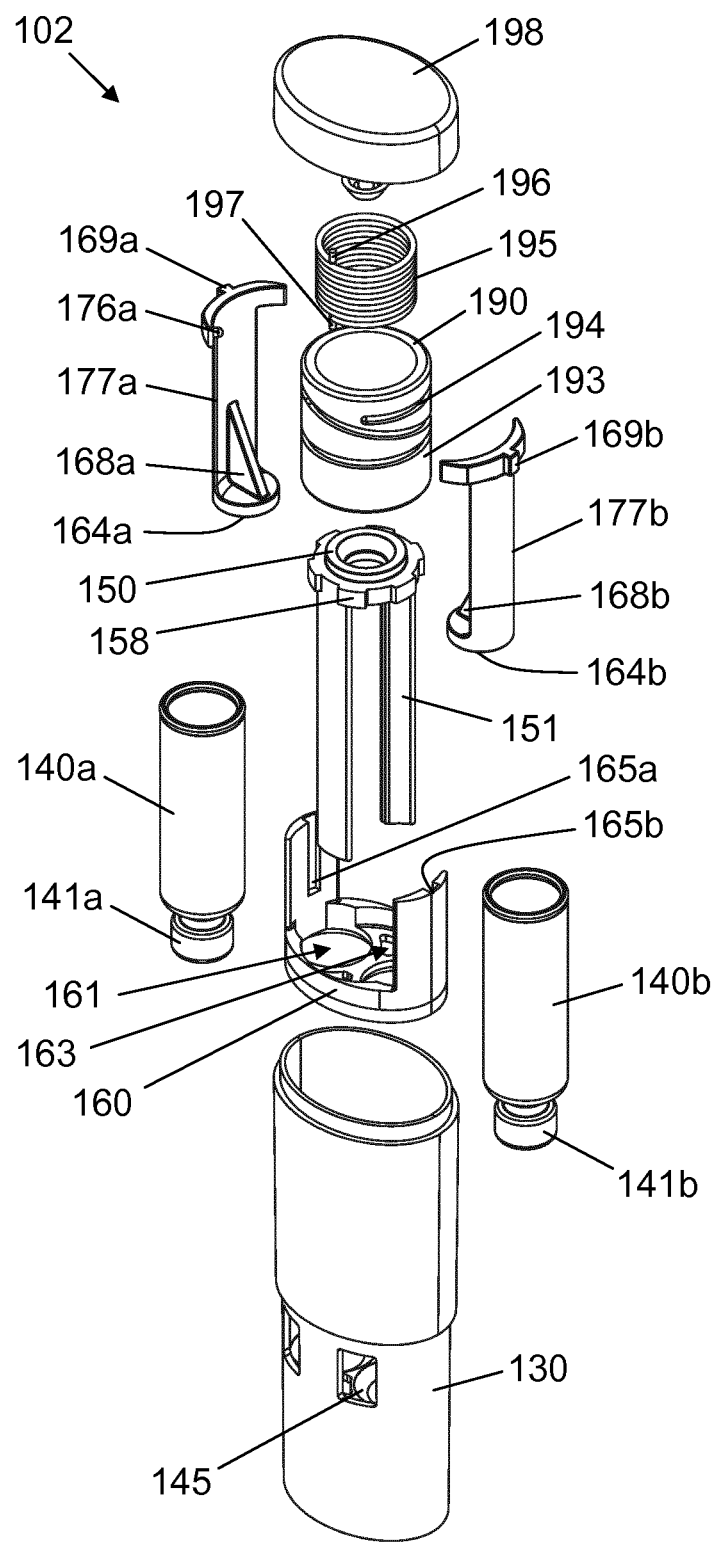
FIG. 23 is an exploded view of a drug delivery device according to another embodiment of the invention.

FIG. 23 is an exploded view of an injection device 102 according to another embodiment of the invention. The injection device 102 is adapted to deliver respective substances from a first cartridge 140a, having a first outlet portion 141a, and a second cartridge 140b, having a second outlet portion 141b, sequentially through a single needle interface (not shown).

The injection device 102 comprises a housing 130 with an integrated cartridge chassis 145, supporting respective distal portions of the first cartridge 140a and the second cartridge 140b in a side-by-side arrangement. An insert 160 supporting respective proximal end portions of the cartridges 140a, 140b is immovably arranged in a proximal portion of the housing 130. The insert 160 comprises a first longitudinal groove 165a and a second longitudinal groove 165b, and a pair of opposite openings 163 adapted to slidably receive respective legs 151 of a transfer element 150 in a manner which rotationally interlocks the insert 160 and the transfer element 150. The transfer element 150 further comprises a toothed coupling ring 158 to which each leg 151 is attached.

The housing 130 also accommodates a first piston rod 177a and a second piston rod 177b. The first piston rod 177a comprises a first outer protrusion 169a which is slidably engaged with the first longitudinal groove 165a, thereby rendering the first piston rod 177a axially movable but rotationally fixed with respect to the housing 130, and the second piston rod 177b comprises a second outer protrusion 169b which is slidably engaged with the second longitudinal groove 165b, thereby rendering the second piston rod 177b axially movable but rotationally fixed with respect to the housing 130. The first piston rod 177a further comprises a first inner protrusion 176a, a first stabilising plate 168a, and a first piston rod foot 164a adapted to interact with and displace a first piston 143a (see FIG. 24) in the first cartridge 140a. Similarly, the second piston rod 177b further comprises a second inner protrusion 176b (see FIG. 27), a second stabilising plate 168b, and a second piston rod foot 164b adapted to interact with and displace a second piston 143b (see FIG. 24) in the second cartridge 140b.

A rotatable drum 190 is arranged between the first piston rod 177a and the second piston rod 177b and comprises a cylindrical exterior surface 193 on which is provided a groove 194. Both the first inner protrusion 176a and the second inner protrusion 176b are slidably received in the groove 194, whereby movement of the rotatable drum 190 affects the respective axial positions of the first piston rod 177a and the second piston rod 177b in a predefined manner, as will be clear from the below. The toothed coupling ring 158 fits within a distal portion of the rotatable drum 190 and is axially displaceable therein from a pre-use position in which the rotatable drum 190 and the transfer element 150 are rotationally interlocked to a dose release position in which the rotatable drum 190 is free to rotate relative to the transfer element 150.

A pre-tensioned torsion spring 195 is arranged within a proximal portion of the rotatable drum 190 and has a distal spring end 197 attached to an interior surface of the rotatable drum 190 and a proximal spring end 196 attached to a top cap 198 immovably attached to the housing 130. The pre-tensioned torsion spring 195 is pre-tensioned to a degree which enables delivery of the entire usable contents of the first cartridge 140a and the second cartridge 140b in one dose expelling action.

FIG. 24 is a longitudinal section view of the injection device 102 before use. It shows the first cartridge 140a and the second cartridge 140b arranged side-by-side in the housing 130. The first cartridge 140a comprises a first chamber 144a being closed by the first piston 143a and a first pierceable septum 142a and containing a first substance. The second cartridge 140b comprises a second chamber 144b being closed by the second piston 143b and a second pierceable septum 142b and containing a second substance.

The housing 130 extends longitudinally beyond the cartridge chassis 145 to define a distal space 139 adapted to receive an injection needle unit (not shown) comprising two rear needles adapted to respectively penetrate the first pierceable septum 142a and the second pierceable septum 142b and a single front needle adapted to penetrate human skin. The injection needle unit is configured to abut the respective distal ends of the legs 151 and to move the entire transfer element 150 proximally during penetration of the first pierceable septum 142a and the second pierceable septum 142b. The result of this movement will be described below with reference to FIG. 25.

The longitudinal section view also shows a harpoon structure 199 extending distally from an interior surface of the top cap 198 towards the toothed coupling ring 158. The harpoon structure 199 is also visible in FIG. 25a which is a longitudinal section perspective view of an assembly comprising of the top cap 198, the pre-tensioned torsion spring 195, the rotatable drum 190, and the transfer element 150. This assembly constitutes a dose release mechanism and supports a very simple handling of the injection device 102, as will be explained in the following.

At attachment to the injection device 102 the injection needle unit is in a pre-use position in the distal space 139 in which the two rear needles are spaced apart from the respective first and second pierceable septa 142a, 142b. To perform a dose administration the user simply presses the distal end of the injection device 102 against the skin. This causes the front needle to enter the subcutaneous tissue and the two rear needle to penetrate the respective first and second pierceable septa 142a, 142b and thereby establish fluid connection to the respective first and second chambers 144a, 144b.

The relative axial movement between the housing 130 and the injection needle unit during the insertion of the rear needles into the respective first and second chambers 144a, 144b also causes the legs 151, and the toothed coupling ring 158 being rigidly connected to the legs 151, to be displaced proximally within the housing 130. The toothed coupling ring 158 is thereby moved axially relative to the rotatable drum 190 from the pre-use position depicted in FIG. 25a to the dose release position depicted in FIG. 25b. During this movement the harpoon structure 199 irreversibly passes a circumferential lip 154 on the toothed coupling ring 158, causing the toothed coupling ring 158 to be retained in the dose release position, and the periphery of the toothed coupling ring 158 disengages from a number of protrusions 192 arranged along an inner circumference of the rotatable drum 190, thereby rotationally releasing the rotatable drum 190. As a consequence thereof the pre-tensioned torsion spring 195 releases stored rotational energy to drive the rotatable drum 190 about its own longitudinal axis, causing a sequential expelling of the first substance and the second substance through the injection needle unit and into the skin of the user.

FIG. 26 shows the constructional details of the rotatable drum 190 that enable the sequential expelling of the two substances. FIG. 26a is a first perspective view of the rotatable drum 190, and FIG. 26b is a second perspective view of the rotatable drum 190, turned 180° from the view in FIG. 26a. FIG. 26c is a schematic representation of the groove 194 stretching around the cylindrical exterior surface 193.

The groove 194 stretches between a starting point 194' and a terminal point 194" and comprises a first partly circular track portion 194a extending between the starting point 194' and a first transition point 191', a partly helical track portion 194b extending between the first transition point 191' and a second transition point 191", and a second partly circular track portion 194c extending between the second transition point 191" and the terminal point 194".

FIG. 27 shows the movement pattern of the first piston rod 177a and the second piston rod 177b during rotation of the rotatable drum 190. Initially, i.e. when delivered from the manufacturer, the second inner protrusion 176b is positioned at the starting point 194' and the first inner protrusion 176a is positioned at the end of the first partly circular track portion 194a just before the first transition point 191'. This is depicted in FIG. 27a.

When the rotatable drum 190 begins to rotate the second inner protrusion 176b thus follows the first partly circular track portion 194a, while the first inner protrusion 176a enters and follows the partly helical track portion 194b. As previously mentioned both the first piston rod 177a and the second piston rod 177b are rotationally locked with respect to the housing 130, so as the first inner protrusion 176a travels the partly helical track portion 194b the first piston rod 177a is displaced axially in the distal direction and the first piston 143a is resultantly pushed a corresponding distance into the first cartridge 140a by the first piston rod foot 164a. However, as the second inner protrusion 176b simultaneously travels the first partly circular track portion 194a the second piston rod 177b remains stationary within the housing 130. In FIG. 27b the rotatable drum 190 has turned 90°, and a resultant axial displacement of the first piston rod 177a can be seen.

In FIG. 27c the rotatable drum 190 has turned 270° which has brought the first inner protrusion 176a to the second transition point 191" and the second inner protrusion 176b to the first transition point 191'. The first piston rod 177a has thereby been fully axially displaced and the first cartridge 140a has accordingly been emptied. Notably, the second piston rod 177b has not yet experienced any axial displacement.

Now, further rotation of the rotatable drum 190 causes the second inner protrusion 176b to enter the partly helical track portion 194b and the first inner protrusion 176a to enter the second partly circular track portion 194c. This is depicted in FIG. 27d. As the rotation continues the second inner protrusion 176b travels the partly helical track portion 194b past the second transition point 191" and just into the second partly circular track portion 194c, while the first inner protrusion 176a travels the second partly circular track portion 194c to the terminal point 194". The second piston rod 177b is thereby displaced axially in the distal direction, and the second piston 143b is resultantly pushed a corresponding distance into the second cartridge 140b by the second piston rod foot 164b, while the first piston rod 177a remains stationary within the housing 130.

When the first inner protrusion 176a reaches the terminal point 194" the rotatable drum 190 stops and the dose delivery process is over. At this point also the second piston rod 177b has been fully axially displaced and the second cartridge 140b accordingly emptied. The sequential dosing of the first substance and the second substance has thus been completed, and the user can subsequently retract the front needle from the skin and discard the injection device 102 together with the injection needle unit.

The three track portions of the groove 194 are selected in accordance with the desired total dose to be expelled from the injection device 102, with the pitch of the partly helical track portion 194b deciding the axial displacement of the first piston 143a and the second piston 143b. In order to execute the sequential dosing the rotatable drum 190 thus undergoes a predetermined movement about its own longitudinal axis. During a first part of said predetermined movement, carried out from FIG. 27a to FIG. 27c, the first piston rod 177a is displaced axially relative to the housing 130 while the second piston rod 177b remains stationary, and during a second part of said predetermined movement, carried out from FIG. 27c to FIG. 27e, the second piston rod 177b is displaced axially relative to the housing 130 while the first piston rod 177a remains stationary.

The shown sequential dose expelling mechanism enables a very compact and simple to handle injection device. The injection needle unit may even be pre-attached to the injection device 102 by the manufacturer, whereby the user only needs to press the housing 130 against the skin in order to connect the rear needles to the respective first and second chambers 144a, 144b and release the pre-tensioned torsion spring 195 to actuate the rotatable drum 190 through the predetermined movement in one uninterrupted stroke.

The invention claimed is:

1. A drug delivery device for sequential administration of substances, comprising:
    a first variable volume reservoir holding a first substance and comprising a first outlet and a first displaceable wall,
    a second variable volume reservoir holding a second substance and comprising a second outlet and a second displaceable wall,
    a first wall actuation structure activatable to move the first displaceable wall and thereby expel a dose of the first substance through the first outlet,
    a second wall actuation structure activatable to move the second displaceable wall and thereby expel a dose of the second substance through the second outlet, and a drive structure for activating the first wall actuation structure and the second wall actuation structure, wherein the drive structure is configured to perform a predetermined movement during one sequential administration of the first substance and the second substance, the predetermined movement comprising a first part movement followed by a second part movement, wherein the drive structure is configured to activate the first wall actuation structure during the first part movement and to activate the second wall actuation structure during the second part movement, wherein the drive structure is operatively coupled with the first wall actuation structure and decoupled from the second wall actuation structure during the first part movement and operatively coupled with the second wall actuation structure and decoupled from the first wall actuation structure during the second part movement, and a torsion spring operatively coupled with the drive structure and adapted to release rotational energy to cause the drive structure to perform the predetermined movement.

2. The drug delivery device according to claim 1, wherein the predetermined movement is uninterrupted.

3. The drug delivery device according to claim 1, further comprising a housing extending along a longitudinal housing axis and accommodating, at least partly, the first wall actuation structure and the second wall actuation structure, wherein the drive structure is axially fixed with respect to the housing during the predetermined movement.

4. The drug delivery device according to claim 1, wherein the first wall actuation structure comprises a first set of teeth and the second wall actuation structure comprises a second set of teeth, and wherein the drive structure comprises a plurality of teeth configured for sequential engagement with the first set of teeth and the second set of teeth.

5. The drug delivery device according to claim 4, wherein the drive structure comprises a cylindrical surface and the plurality of teeth are distributed on the cylindrical surface.

6. The drug delivery device according to claim 5, wherein the drive structure extends along a longitudinal drive structure axis, wherein the first wall actuation structure and the second wall actuation structure are capable of engagement with the drive structure in a number of different axial positions of the first set of teeth and the second set of teeth relative to the cylindrical surface, and wherein the number of different axial positions correspond to the number of settable doses on the predefined dose setting scale.

7. The drug delivery device according to claim 6, wherein in each of the number of different axial positions the first set of teeth and the second set of teeth are adapted to sequentially engage with a dose specific number of the plurality of teeth on the drive structure.

8. The drug delivery device according to claim 6, wherein the cylindrical surface is an inner surface oriented radially inwardly, and wherein the first set of teeth and the second set of teeth are axially displaceable within a space surrounded by the inner surface.

9. The drug delivery device according to claim 8, wherein the plurality of teeth are arranged such that during one sequential administration of the first substance and the second substance a first engaging tooth will engage with the second set of teeth immediately after a last engaging tooth disengages from the first set of teeth.

10. The drug delivery device according to claim 4, wherein the drive structure forms part of a user operable dose setting mechanism and an extent of the predetermined movement is selectable by the user in accordance with a predefined dose setting scale.

11. The drug delivery device according to claim 10, wherein the drive structure comprises a plurality of dose related indicia.

12. A drug delivery device for sequential administration of substances, comprising:

a first variable volume reservoir holding a first substance and comprising a first outlet and a first displaceable wall, a second variable volume reservoir holding a second substance and comprising a second outlet and a second displaceable wall, a first wall actuation structure activatable to move the first displaceable wall and thereby expel a dose of the first substance through the first outlet, a second wall actuation structure activatable to move the second displaceable wall and thereby expel a dose of the second substance through the second outlet, and a drive structure for activating the first wall actuation structure and the second wall actuation structure, wherein the drive structure is configured to perform a predetermined movement during one sequential administration of the first substance and the second substance, the predetermined movement comprising a first part movement followed by a second part movement, wherein the drive structure is configured to activate the first wall actuation structure during the first part movement and to activate the second wall actuation structure during the second part movement, wherein the first wall actuation structure comprises a first set of teeth and the second wall actuation structure comprises a second set of teeth, wherein the drive structure comprises a plurality of teeth configured for sequential engagement with the first set of teeth and the second set of teeth, and wherein the drive structure is operatively coupled with the first wall actuation structure and decoupled from the second wall actuation structure during the first part movement and operatively coupled with the second wall actuation structure and decoupled from the first wall actuation structure during the second part movement.

13. The drug delivery device according to claim 12, wherein the predetermined movement is uninterrupted.

14. The drug delivery device according to claim 12, further comprising a housing extending along a longitudinal housing axis and accommodating, at least partly, the first wall actuation structure and the second wall actuation structure, wherein the drive structure is axially fixed with respect to the housing during the predetermined movement.

15. The drug delivery device according to claim 14, further comprising a torsion spring operatively coupled with the drive structure and adapted to release rotational energy to cause the drive structure to perform the predetermined movement.

16. The drug delivery device according to claim 12, wherein the drive structure comprises a cylindrical surface and the plurality of teeth are distributed on the cylindrical surface.

17. The drug delivery device according to claim 16, wherein the drive structure extends along a longitudinal drive structure axis, wherein the first wall actuation structure and the second wall actuation structure are capable of engagement with the drive structure in a number of different axial positions of the first set of teeth and the second set of teeth relative to the cylindrical surface, and wherein the number of different axial positions correspond to the number of settable doses on the predefined dose setting scale.

18. The drug delivery device according to claim 17, wherein in each of the number of different axial positions the first set of teeth and the second set of teeth are adapted to sequentially engage with a dose specific number of the plurality of teeth on the drive structure.

19. The drug delivery device according to claim 17, wherein the cylindrical surface is an inner surface oriented radially inwardly, and wherein the first set of teeth and the second set of teeth are axially displaceable within a space surrounded by the inner surface.

20. The drug delivery device according to claim 19, wherein the plurality of teeth are arranged such that during one sequential administration of the first substance and the second substance a first engaging tooth will engage with the second set of teeth immediately after a last engaging tooth disengages from the first set of teeth.

21. The drug delivery device according to claim 12, wherein the drive structure forms part of a user operable dose setting mechanism and the extent of the predetermined movement is selectable by the user in accordance with a predefined dose setting scale.

22. The drug delivery device according to claim 21, wherein the drive structure comprises a plurality of dose related indicia.

* * * * *